United States Patent
Sieg et al.

(10) Patent No.: US 8,138,304 B2
(45) Date of Patent: Mar. 20, 2012

(54) NEURAL REGENERATION PEPTIDES AND FORMULATIONS THEREOF

(75) Inventors: Frank Sieg, Auckland (NZ); Margaret Anne Brimble, Auckland (NZ); Victoria Justine Muir, Auckland (NZ)

(73) Assignee: Neuren Pharmaceuticals Limited, Auckland (NZ)

( * ) Notice: Subject to any disclaimer, the term of this patent is extended or adjusted under 35 U.S.C. 154(b) by 583 days.

(21) Appl. No.: 11/919,952

(22) PCT Filed: May 5, 2006

(86) PCT No.: PCT/US2006/017534
§ 371 (c)(1),
(2), (4) Date: Mar. 16, 2009

(87) PCT Pub. No.: WO2006/121926
PCT Pub. Date: Nov. 16, 2006

(65) Prior Publication Data
US 2010/0130410 A1    May 27, 2010

Related U.S. Application Data

(60) Provisional application No. 60/678,304, filed on May 6, 2005, provisional application No. 60/726,904, filed on Oct. 14, 2005, provisional application No. 60/772,947, filed on Feb. 14, 2006.

(51) Int. Cl.
*A61K 38/00* (2006.01)
*A61K 38/14* (2006.01)
*A61K 38/04* (2006.01)
*C07K 4/00* (2006.01)
*C07K 7/00* (2006.01)
*C07K 7/04* (2006.01)
*C07K 7/06* (2006.01)
*C07K 7/08* (2006.01)
*C07K 9/00* (2006.01)

(52) U.S. Cl. ........ 530/300; 530/322; 530/327; 530/328; 530/333; 530/335

(58) Field of Classification Search ........................ None
See application file for complete search history.

(56) References Cited

U.S. PATENT DOCUMENTS

| 7,563,862 B2 * | 7/2009 | Sieg et al. | 530/300 |
| 7,767,786 B2 * | 8/2010 | Sieg et al. | 530/300 |
| 2003/0211990 A1 * | 11/2003 | Sieg et al. | 514/12 |
| 2005/0131212 A1 * | 6/2005 | Sieg et al. | 530/350 |
| 2010/0130410 A1 * | 5/2010 | Sieg et al. | 514/12 |

OTHER PUBLICATIONS

U.S. Appl. No. 12/849,681, filed Aug. 2010, Sieg et al.*
Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
Burgess et al. J of Cell Biol. 1990. 111:2129-2138.*
Bowie et al. Science, 1990, 247:1306-1310.*
Pawson et al. 2003, Science 300:445-452.*

* cited by examiner

*Primary Examiner* — Chang-Yu Wang
(74) *Attorney, Agent, or Firm* — Nixon & Vanderhye

(57) ABSTRACT

Neural regeneration peptide consisting of a sequence comprised in the sequence of REGRRAAPGRAGG(SEQ ID NO:1).

6 Claims, 14 Drawing Sheets

SEQUENCE LISTING

```
<160> NUMBER OF SEQ ID NOS: 20

<210> SEQ ID NO 1
<211> LENGTH: 13
<212> TYPE: PRT
<213> ORGANISM: Homo sapiens
<220> FEATURE:
<221> NAME/KEY: MUTAGEN
<222> LOCATION: (13)..(13)
<223> OTHER INFORMATION: AMIDATION

<400> SEQUENCE: 1

Arg Glu Gly Arg Arg Ala Ala Pro Gly Arg Ala Gly Gly
1               5                   10

<210> SEQ ID NO 2
<211> LENGTH: 11
<212> TYPE: PRT
<213> ORGANISM: Homo sapiens
<220> FEATURE:
<221> NAME/KEY: MUTAGEN
<222> LOCATION: (11)..(11)
<223> OTHER INFORMATION: AMIDATION

<400> SEQUENCE: 2

Gly Arg Arg Ala Ala Pro Gly Arg Ala Gly Gly
1               5                   10

<210> SEQ ID NO 3
<211> LENGTH: 13
<212> TYPE: PRT
<213> ORGANISM: Homo sapiens

<400> SEQUENCE: 3

Arg Glu Gly Arg Arg Asp Ala Pro Gly Arg Ala Gly Gly
1               5                   10

<210> SEQ ID NO 4
<211> LENGTH: 25
<212> TYPE: PRT
<213> ORGANISM: Homo sapiens

<400> SEQUENCE: 4

Gly Thr Pro Gly Arg Ala Glu Ala Gly Gly Gln Val Ser Pro Cys Leu
1               5                   10                  15

Ala Ala Ser Cys Ser Gln Ala Tyr Gly
            20                  25

<210> SEQ ID NO 5
<211> LENGTH: 24
<212> TYPE: PRT
<213> ORGANISM: Mus musculus

<400> SEQUENCE: 5

Ser Glu Pro Glu Ala Arg Arg Ala Pro Gly Arg Lys Gly Gly Val Val
1               5                   10                  15

Cys Ala Ser Leu Ala Ala Asp Trp
            20

<210> SEQ ID NO 6
<211> LENGTH: 21
<212> TYPE: PRT
```

<213> ORGANISM: Rattus norvegicus

<400> SEQUENCE: 6

Met Glu Val Gly Trp Tyr Arg Ser Pro Phe Ser Arg Val Val His Leu
1               5                   10                  15

Tyr Arg Asn Gly Lys
            20

<210> SEQ ID NO 7
<211> LENGTH: 19
<212> TYPE: PRT
<213> ORGANISM: Homo sapiens

<400> SEQUENCE: 7

Arg Arg Ala Pro Gly Ser Leu His Pro Cys Leu Ala Ala Ser Cys Ser
1               5                   10                  15

Ala Ala Gly

<210> SEQ ID NO 8
<211> LENGTH: 11
<212> TYPE: PRT
<213> ORGANISM: Homo sapiens

<400> SEQUENCE: 8

Asp Lys Pro Glu Ala Arg Arg Ala Pro Gly Ser
1               5                   10

<210> SEQ ID NO 9
<211> LENGTH: 25
<212> TYPE: PRT
<213> ORGANISM: Homo sapiens

<400> SEQUENCE: 9

Gly Thr Pro Gly Arg Ala Glu Ala Gly Gly Gln Val Ser Pro Cys Leu
1               5                   10                  15

Ala Ala Ser Cys Ser Gln Ala Tyr Gly
            20                  25

<210> SEQ ID NO 10
<211> LENGTH: 9
<212> TYPE: PRT
<213> ORGANISM: Homo sapiens

<400> SEQUENCE: 10

Gly Thr Pro Gly Arg Ala Glu Ala Gly
1               5

<210> SEQ ID NO 11
<211> LENGTH: 9
<212> TYPE: PRT
<213> ORGANISM: Homo sapiens

<400> SEQUENCE: 11

Thr Pro Gly Arg Ala Glu Ala Gly Gly
1               5

<210> SEQ ID NO 12
<211> LENGTH: 9
<212> TYPE: PRT
<213> ORGANISM: Homo sapiens

<400> SEQUENCE: 12

Gly Arg Ala Glu Ala Gly Gly Gln Val
1               5

<210> SEQ ID NO 13
<211> LENGTH: 9
<212> TYPE: PRT
<213> ORGANISM: Homo sapiens

<400> SEQUENCE: 13

Arg Ala Glu Ala Gly Gly Gln Val Ser
1               5

<210> SEQ ID NO 14
<211> LENGTH: 7
<212> TYPE: PRT
<213> ORGANISM: Homo sapiens

<400> SEQUENCE: 14

Gly Arg Ala Glu Ala Gly Gly
1               5

<210> SEQ ID NO 15
<211> LENGTH: 12
<212> TYPE: PRT
<213> ORGANISM: Homo sapiens

<400> SEQUENCE: 15

Ser Glu Pro Phe Glu Ala Arg Arg Ala Pro Gly Arg
1               5                   10

<210> SEQ ID NO 16
<211> LENGTH: 9
<212> TYPE: PRT
<213> ORGANISM: Mus musculus

<400> SEQUENCE: 16

Ser Glu Pro Glu Ala Arg Arg Ala Pro
1               5

<210> SEQ ID NO 17
<211> LENGTH: 9
<212> TYPE: PRT
<213> ORGANISM: Mus musculus

<400> SEQUENCE: 17

Glu Pro Glu Ala Arg Arg Ala Pro Gly
1               5

<210> SEQ ID NO 18
<211> LENGTH: 9
<212> TYPE: PRT
<213> ORGANISM: Mus musculus

<400> SEQUENCE: 18

Pro Glu Ala Arg Arg Ala Pro Gly Arg
1               5

<210> SEQ ID NO 19
<211> LENGTH: 9
<212> TYPE: PRT
<213> ORGANISM: Mus musculus

<400> SEQUENCE: 19

Glu Ala Arg Arg Ala Pro Gly Arg Lys
1               5

<210> SEQ ID NO 20

```
<211> LENGTH: 9
<212> TYPE: PRT
<213> ORGANISM: Mus musculus

<400> SEQUENCE: 20

Ala Arg Arg Ala Pro Gly Arg Lys Gly
1               5
```

NEURAL REGENERATION PEPTIDES AND FORMULATIONS THEREOF

CLAIM OF PRIORITY

This application claims priority to PCT International Application No: PCT/US2006/017534, filed 5 May 2006 which claims priority to U.S. Provisional Patent Application No. 60/678,304 filed May 6, 2005, entitled "Neural Regeneration Peptides and Methods for Their Use in Prevention of Obstetric Complications," Inventor: Frank Sieg, now abandoned; U.S. Provisional Patent Application No. 60/726,904 filed Oct. 14, 2005, entitled: "Neural Regeneration Peptides and Methods for Their Use in Treatment of Autoimmune Disorders of the Brain," Inventor: Frank Sieg, now abandoned; and U.S. Provisional Patent Application No. 60/772,947 filed Feb. 14, 2006, entitled: "Neural Regeneration Peptides and Methods for Their Use in Prevention and Treatment of Peripheral Neuropathy," Inventor: Frank Sieg, now abandoned. Each of the aforementioned applications is herein expressly incorporated fully by reference, as if separately so incorporated.

FIELD OF THE INVENTION

This invention is directed to compositions and methods for the use of oligonucleotides and peptides that promote migration, proliferation, survival, differentiation, and/or outgrowth of neural and trophoblast cells. More specifically, this invention is directed to the use of such peptides in the treatment of brain injury, neurodegenerative disease and/or obstetric complications.

BACKGROUND

Related Art

Mild to severe traumatic brain injury (TBI), focal or global ischemia and neurological insults and disorders can result in significant neuronal cell loss and loss of brain function within a short time period after an insult. There are few treatments currently available to prevent cell death that occurs in the brain as a consequence of head injury or damage caused by disease. To date, there are also few treatments available to restore neuronal function. Treatments available at present for chronic neurodegenerative diseases such as Alzheimer's disease, Parkinson's disease, Huntington's disease and Multiple Sclerosis only target symptoms. Few drugs are currently available to intervene in the disease process or prevent cell death. Similarly, there are few treatments available for prevention or treatment of obstetric complications involving trophoblast survival.

To address the needs, the inventor and others have previously discovered and described oligonucleotides and peptides that promote neuronal migration, proliferation, survival, differentiation, and/or neurite outgrowth, NRPs (U.S. patent application Ser. No. 10/225,838 and U.S. patent application Ser. No. 10/976,699), expressly incorporated herein fully by reference.

However, there is still a need in the art to identify new NRPs and to find new therapies for treating acute and chronic neurological disorders and disorders of trophoblast cells.

SUMMARY OF THE INVENTION

Embodiments of this invention include novel neural regeneration peptides (NRPs). Other embodiments of this invention include the methods for the use of the novel NRPs to promote neuronal migration, neurite outgrowth, neuronal proliferation, neural differentiation, neuronal survival and/or trophoblast proliferation, migration and survival.

Additional embodiments of this invention include methods for use of NRPs in preventing degeneration or death of peripheral neurons.

Further embodiments of this invention include methods for the use of NRPs in the treatment of pre-eclampsia, HELLP or IUGR. Such embodiments include peptides that can induce the migration or survival of trophoblasts. Other embodiments of this invention include methods for use of NRPs to decrease TNF-alpha- and interferon-gamma-induced injury in vitro in both placental trophoblast cells, making them suitable for treating obstetric complications.

Additional embodiments include use of NRPs to treat autoimmune disorders of the brain.

BRIEF DESCRIPTION OF THE FIGURES

This invention is described by way of description of particular embodiments thereof. Other objects, features and advantages of embodiments of this invention will become apparent from the specification and the figures, in which:

FIG. 1 shows the effects of NRP-5 segment RG analogue D6A on neuroprotective activity over a broad dosage range of from 0.1 fM to 100 nM. Student's t-test was used for statistical analysis (*** $p<0.001$, N=4).

FIG. 3A shows that NRP-5 segment RG analogue D6A (SEQ ID NO:1) exhibited chemoattractive properties in attracting neuronal stem cells ("NSCs") under physiological (injury-free) conditions, as shown with a haptotactic migration assay. 55.4% more cells were migrating in the NRP condition. Student's t-test was used for statistical analysis ( $p<0.01$, N=6). FIG. 3B shows that NRP-5 segment RG analogue D6A (SEQ ID NO:1) promotes migration into an activated astroglial monolayer, a condition that mimics CNS injury conditions as they occur during SCI. 69.1% more stem cells migrated in the NRP condition. Student's t-test was used for statistical analysis (* $p<0.001$, N=5).

DETAILED DESCRIPTION

Figure 1:
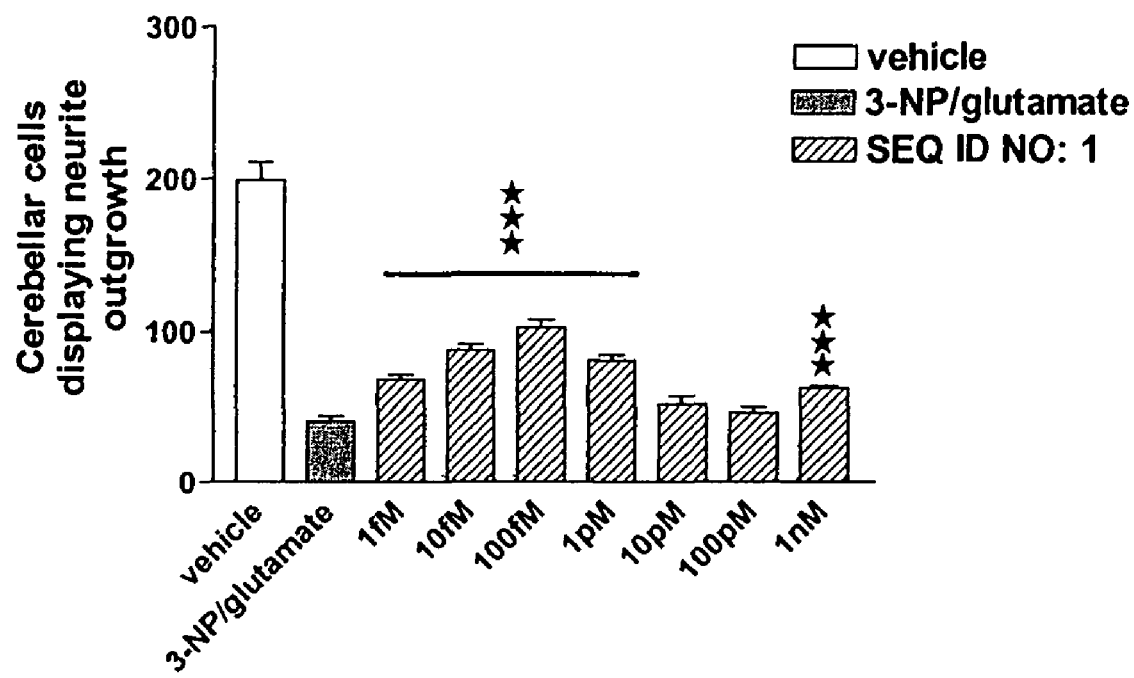
FIG. 1 depicts neuronal survival and proliferation induction by NRP-5 segment RG analogue D6A (SEQ ID NO:1).

Embodiments of this invention include the use of Neural Regeneration Peptides (NRPs) previously disclosed in U.S. patent application Ser. No. 10/225,838 titled "Neural Regeneration Peptides and Methods for Their Use in Treatment of Brain Damage" filed Aug. 22, 2002, Publication No: US 2003/0211990; Ser. No. 10/976,699 titled, "Neural Regeneration Peptides and Methods for Their Use in Treatment of Brain Damage" filed Oct. 29, 2004; U.S. 60/678,302 titled "Neural Regeneration Peptides and Methods for Their Use in Preventing Obstetric Complications" filed May 6, 2005; U.S. 60/699,642 titled "Neural Regeneration Peptides and Antioxidants Protect Neurons From Degeneration" filed Jul. 15, 2005; U.S. 60/714,916 titled "Neural Regeneration Peptides and Antioxidants Protect Neurons from Degeneration" filed Sep. 7, 2005; U.S. 60/726,904 titled "Neural Regeneration Peptides and Methods for Their Use in Treatment of Autoimmune Disorders of the Brain" filed Oct. 14, 2005; PCT International Patent Applications: PCT/US02/26782 titled "Neural Regeneration Peptides and Methods for Their Use in Treatment of Brain Damage" filed Aug. 22, 2002, Publication No: WO 03/018754; and PCT/US2004/036203 titled "Neural Regeneration Peptides and Methods for Their Use in Treatment of Brain Damage" filed Nov. 1, 2004, Publication No: WO 2005/042,561; all for prevention of degeneration or death of neurons and other cell types. Each of the aforementioned patent applications is expressly incorporated herein fully by reference.

DEFINITIONS

The term "homolog" includes one or more genes whose gene sequences are significantly related because of an evolutionary relationship, either between species (ortholog) or within a species (paralog). Homolog also includes genes related by descent from a common ancestral DNA sequence. Homolog also includes a relationship between genes separated by a speciation event, or to a relationship between genes by the event of genetic duplication (see paralog). As used herein, the term "homolog" also includes gene products related to each other by way of an evolutionary relationship. NRPs having conserved amino acid sequence domains are examples of homologs.

The term "paralog" includes one of a set of homologous genes that have diverged from each other as a consequence of genetic duplication. For example, the mouse alpha globin and beta globin genes are paralogs. As used herein, the term "paralog" also includes gene products related to each other by way of an evolutionary relationship. Human NRPs having conserved amino acid sequence domains are examples of paralogs.

The term "ortholog" includes one of a set of homologous genes that have diverged from each other as a consequence of speciation. For example, the alpha globin genes of mouse and chick are orthologs. As used herein, the term "ortholog" also includes gene products related to each other by way of an evolutionary relationship. Human and mouse NRPs having conserved amino acid sequence domains are examples of homologs.

The term "paralog peptide" includes a peptide encoded by a paralog nucleotide sequence.

The term "peptide" and "protein" include polymers made of amino acids.

The term "prodrug" includes molecules, including pro-peptides which, following enzymatic, metabolic or other processing, result in an active NRP, an active NRP analog or a NRP paralog.

The term "NRP compound" includes NRPs, NRP homologs, NRP paralogs, NRP orthologs, NRP analogs, and prodrugs of NRP.

The term "NRP" includes peptides having functions including one or more of neural migration, neuroblast migration, neural proliferation, neuronal differentiation, neuronal survival and neurite outgrowth, regardless of evolutionary relationship. The term NRP also refers to peptides having sequences defined herein. It is understood that a "sequence" or "SEQ ID NO:" includes both C-terminal OH and C-terminal amidated peptides.

Amino acids are represented by the standard symbols where alanine is represented by "A" or "Ala", arginine by "R" or "Arg", asparagine by "N" or "Asn", aspartic acid by "D" or "Asp", cysteine by "C" or "Cys", glutamic acid by "E" or "Glu", glutamine by "Q" or "Gln", glycine by "G" or "Gly", histidine by "H" or "His", isoleucine by "I" or "Ile", leucine by "L" or "Leu", lysine by "K" or "Lys", methionine by "M" or "Met", phenylalanine by "F" or "Phe", proline by "P" or "Pro", serine by "S" or "Ser", threonine by "T" or "Thr", tryptophan by "W" or "Trp", tyrosine by "Y" or "Tyr", and valine by "V" or "Val". Carboxy terminally amidated peptides are indicated by —NH$_2$.

"Disease" includes any unhealthy condition of CNS or peripheral nervous system of an animal, including particularly Parkinson's disease, Lewy Body, Huntington's disease, Alzheimer's disease, multiple sclerosis, motor neuron disease, muscular dystrophy, peripheral neuropathies, metabolic disorders of the nervous system including glycogen storage diseases.

"Insult" includes any disease or injury that can cause a brain or other cell to degenerate or die.

"Injury" includes any acute damage of an animal, including particularly stroke, traumatic brain injury, hypoxia, ischemia, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycaemia and status epilepticus, episodes of cerebral asphyxia associated with coronary bypass surgery, hypotensive episodes and hypertensive crises, cerebral trauma and spinal cord injury.

DESCRIPTION OF SPECIFIC EMBODIMENTS

Certain embodiments of this invention include compositions and methods for the treatment of brain damage, comprising administering neural regeneration peptides (NRPs) to mammals in need of such treatment.

NRPs are characterized by the presence of one or more peptide domains, including a [A]PG[R,S] domain, such as APGS, APG, APGR, APGS, PGR or PGS. Additionally, NPRs may have other domains, including ARG, ARR, a C-terminal GG domain, an [A,G]RR domain, including ARR or GRR domain. NRPs may also have a PE domain. Thus, NRPs may have one or more of the above domains.

A series of NRPs was described in U.S. patent application Ser. Nos. 10/225,838 and 10/976,699. One of those NRPs, NRP-5 (SEQ ID NO: 11 in U.S. Ser. No. 10/976,669), includes the single letter amino acid sequence REGR-RDAPGRAGG (SEQ ID NO:30 in U.S. Ser. No. 10/976,669; and also called "NRP-5RG") was used to develop a novel 13-mer NRP analogue having the amino acid sequence REGRRDAPGRAGG (SEQ ID NO:1; also called "NRP-5RG D6A" or "NRP-5RG analogue D6A"), comprising the sequence:

```
REGRRAAPGRAGG-NH₂        SEQ ID NO: 1
```

SEQ ID NO:1 has a GRR domain, a APGR domain and a C-terminal GG domain.

Another embodiment of the invention is an 11-mer analogue of NRP-5 (SEQ ID NO: 11 in U.S. patent application Ser. No. 10/976,699), herein termed NRP-5 segment GG analogue D4A, comprising the following sequence:

```
GRRAAPGRAGG-NH₂          SEQ ID NO: 2
```

SEQ ID NO:2 has a GRR domain, an APG domain and a C-terminal GG domain.

Additional embodiments of the invention include use of NRPs to treat functional neurological deficits resulting from autoimmune disorders of the brain, including multiple sclerosis. In certain of these embodiments, several NRPs were found to be effective.

A 13-mer NRP-5 segment RG (also known as SEQ ID NO: 30 disclosed in U.S. patent application Ser. No. 10/976,699) is

```
REGRRDAPGRAGG            SEQ ID NO: 3
```

As with SEQ ID NO:1 and SEQ ID NO:2, SEQ ID NO:3 has a GRR domain, an APGR domain and a C-terminal GG domain.

Additionally, an NPP, herein called 25-mer NRP-4 GG, also known as (SEQ ID NO: 29 disclosed in U.S. patent application Ser. No. 10/976,699) is

```
GTPGRAEAGGQVSPCLAASCSQAYG    SEQ ID NO: 4
```

24-mer NRP-7 SW, also known as SEQ ID NO: 24 in U.S. patent application Ser. No. 10/976,699 is

```
SEPEARRAPGRKGGVVCASLAADW     SEQ ID NO: 5
``` are useful.

We studied the effects of NRPs on mice with induced experimental autoimmune encephalitis (EAE) a recognized model of the human disorder, multiple sclerosis. To produce EAE, a 200 µL of an emulsion containing 200 µg of the encephalitogenic peptide MOG35-55

```
MEVGWYRSPFSRVVHLYRNGK        SEQ ID NO: 6
```

Additional NRPs of this invention include:

```
RRAPGSLHPCLAASCSAAG          SEQ ID NO: 7
DKPEARRAPGS                  SEQ ID NO: 8
GTPGRAEAGGQVSPCLAASCSQAYG    SEQ ID NO: 9
GTPGRAEAG                    SEQ ID NO: 10
TPGRAEAGG                    SEQ ID NO: 11
GRAEAGGQV                    SEQ ID NO: 12
RAEAGGQVS                    SEQ ID NO: 13
GRAEAGG                      SEQ ID NO: 14
SEPFEARRAPGR                 SEQ ID NO: 15
SEPEARRAP                    SEQ ID NO: 16
EPEARRAPG                    SEQ ID NO: 17
PEARRAPGR                    SEQ ID NO: 18
EARRAPGRK                    SEQ ID NO: 19
ARRAPGRKG                    SEQ ID NO: 20
```

Certain embodiments of this invention include use of NRPs to prevent degeneration or death of peripheral neurons. In certain of these embodiments, the NRP-5 segment GG analogue D4A (SEQ ID NO:2) was found to be effective.

Other embodiments include the use of NRPs to treating disorders involving reduced trophoblast migration including pre-eclampsia, HELLP or IUGR. Such embodiments include peptides that can induce the migration or survival of trophoblasts (for example, SEQ ID NO: 1).

We also unexpectedly found that NRPs can decrease TNF-alpha- and interferon-gamma-induced injury in vitro in both human term placental trophoblast cells and in a placental cell line (for example, SEQ ID NO: 1).

It can be appreciated that NRPs can be effective either as C-terminal free OH peptides or as C-amidated peptides. Both free C-terminal OH peptides and C-terminal amidated peptides are effective, and both are included within the scope of this invention.

Therapeutic Uses of NRP Compounds

NRPs of this invention can be used to treat neurological disorders and obstetric complications. NPRs have been unexpectedly effective in treating neural degeneration associated with autoimmune disorders of the brain, peripheral neuropathy and toxic injury to neural cells. Additionally NPRs have been unexpectedly effective in promoting survival of trophoblast cells.

Thus, the invention includes embodiments which relate to NRPs, peptides encoded by NRPs, homologs, orthologs or paralogs of NRPs, analogs of NRPs, and prodrugs of NRPs, where a prodrug of an NRP is a molecule that may be enzymatically, metabolically or otherwise modified to become an NRP, a NRP homolog, NRP paralog, an NRP ortholog or an NRP analog. Such molecules are collectively termed as "NRP compounds" or "NRPs." NRP compounds may be encoded for by nucleotide sequences, which may be DNA or RNA and which may be single stranded or double stranded. It will be understood that the invention includes sequences complementary to the sequences described in this application as well as the sequences themselves. It is also to be understood that there may be alternatively spliced forms of NRPs, in which case, those alternatively spliced forms of NRP RNA, and the proteins and peptides they may encode are also considered to be part of this invention.

As indicated above, embodiments of the present invention are based upon the inventors' surprising finding of novel NRPs that can induce neurons and neuroblasts to proliferate, migrate, differentiate, produce neurite outgrowth and can protect neurons against damage caused by neural insults. Proliferation and migration of neural cells into areas of damage caused by acute brain injury or chronic neurodegenerative disease can result in improvement in neural functioning. Further, NRPs can promote neuronal survival, neuronal differentiation, and/or neurite outgrowth. Thus, NRP compounds may be used to treat a variety of disorders and conditions where brain tissue degenerates, is at risk of degeneration or death, or has died.

As indicated above, other embodiments of the present invention are based upon the inventor's surprising finding that NRPs can attenuate motor impairment and body weight loss associated with peripheral neuropathy by preventing degeneration or death of peripheral neurons.

As indicated above, yet other embodiments of the present invention are based upon the inventor's surprising finding that NRPs are useful in treating obstetric complications.

Cells can also use NRP oligonucleotides to stimulate production of NRPs after transfection. In some cases, transfection can be in a replicable vehicle, and in others, the NRP oligonucleotide can be introduced as naked DNA.

Disorders and Conditions Treatable with NRPs

Disorders and conditions in which NRP compounds of this invention can be of benefit include the following.

Nervous System Conditions

Peptides of this invention that have demonstrated effects to promote neural survival, migration or proliferation are indicated in Table 1 below along with their SEQ ID NOs (SID) the length (in mer or amino acid number). Newly disclosed NRPS are indicated by their SID in bold. Presence of certain peptide domains noted above are indicated by underlining.

TABLE 1

| SID | Length (mer) | Sequence | Survival | Migration | Proliferation |
|---|---|---|---|---|---|
| 1 | 13 | REGGRRAAPGRAGG | + | + | + |
| 2 | 11 | GRRAAPGRAGG | + | + | + |
| 3 | 13 | REGRRDAPGRAGG | + | | |
| 4 | 25 | GTPGRAEAGGQVSPCLAASCSQAYG | + | | |
| 5 | 24 | SEPEARRAPGRKGGVVCASLKADW | + | | |
| 7 | 19 | RRAPGSLHPCLAASCSAAG | + | | |
| 8 | 11 | DKPEARRAPGS | (+) | | |
| 9 | 25 | GTPGRAEAGGQVSPCLAASCSQAYG | + | | + |
| 10 | 9 | GTPGRAEAG | − | | |
| 11 | 9 | TPGRAEAGG | + | − | |
| 12 | 9 | GRAEAGGQV | + | + | − |
| 13 | 9 | RAEAGGQVS | − | | |
| 14 | 7 | GRAEAGG | (+) | | |
| 15 | 12 | SEPFEARRAPGR | + | | |
| 16 | 9 | SEPEARRAP | − | | |
| 17 | 9 | EPEARRAPG | | | |
| 18 | 9 | PEARRAPGR | | | |
| 19 | 9 | EARRAPGRK | + | | |
| 20 | 9 | ARRAPGRKG | | | |

Nervous system conditions treatable with NRPs include infections of the central nervous system including bacterial, fungal, spirochetal, parasitic and sarcoid including pyrogenic infections, acute bacterial meningitis, leptomeningitis.

Cerebrovascular diseases include stroke, ischemic stroke, atherosclerotic thrombosis, lacunes, embolism, hypertensive haemorrhage, ruptured aneurysms, vascular malformations, transient ischemic attacks, intracranial haemorrhage, spontaneous subarachnoid haemorrhage, hypertensive encephalopathy, inflammatory diseases of the brain arteries, decreased perfusion caused by, for example, cardiac insufficiency (possibly resulting from coronary bypass surgery) and other forms of cerebrovascular disease.

Craniocerebral traumas include basal skull fractures and cranial nerve injuries, carotid-cavernous fistula, pneumocephalus, aerocele andrhinorrhea, cerebral contusion, traumatic intracerebral haemorrhage, acute brain swelling in children.

Demyelinating diseases include neuromyelitis optica, acute disseminated encephalomyelitis, acute and subacute necrotizing haemorrhagic encephalitis, diffuse cerebral sclerosis of Schilder and multiple sclerosis in conjunction with peripheral neuropathy. Degenerative diseases of the nervous system including syndrome of one or more of progressive dementia, diffuse cerebral atrophy, diffuse cortical atrophy of the non-Alzheimer type, Lewy body dementia, Pick's disease, fronto-temporal dementia, thalamic degeneration, non-Huntingtonian types of Chorea and dementia, cortico-spinal degeneration (Jakob), the dementia-Parkinson-amyotrophic lateral sclerosis complex (Guamanina and others).

Peripheral neuropathy is a common and disabling condition characterised by damage to or loss of peripheral neurons. There are more than 100 types of peripheral neuropathy, each with its own characteristic set of symptoms, pattern of development, and prognosis. Peripheral neuropathy may be either inherited or acquired. Inherited forms of peripheral neuropathy can be caused by genetic mutations. Acquired peripheral neuropathy may result from: physical injury (trauma) to a nerve, tumors, toxins (including chemotherapy), autoimmune responses, nutritional deficiencies, alcoholism, vascular and metabolic disorders (e.g. diabetic neuropathy). The HIV-associated peripheral neuropathy is a common side effect of drugs targeting the reverse transcriptase of the HIV virus. The symptoms of peripheral neuropathy can vary from temporary numbness, tingling, and pricking sensations, sensitivity to touch or muscle weakness, to more extreme symptoms such as burning pain, muscle wasting, paralysis, organ or gland dysfunction.

Metabolic Disorders

Acquired metabolic disorders of the nervous system including metabolic diseases presenting as a syndrome comprising one or more of confusion, stupor or coma-ischemia-hypoxia, hypoglycaemia, hyperglycemia, hypercapnia, hepatic failure and Reye syndrome, metabolic diseases presenting as a progressive extrapyramidal syndrome, metabolic diseases presenting as cerebellar ataxia, hyperthermia, celiac-sprue disease, metabolic diseases causing psychosis or dementia including Cushing disease and steroid encephalopathy, thyroid psychosis and hypothyroidism and pancreatic encephalopathy. An example of a metabolic disorder that can result in neuropathy is pyridoxine excess described more fully below.

Diseases of the nervous system due to nutritional deficiency, alcohol and alcoholism.

Disorders of the nervous system due to drugs and other chemical agents include opiates and synthetic analgesics, sedative hypnotic drugs, stimulants, psychoactive drugs, bacterial toxins, plant poisons, venomous bites and stings, heavy metals, industrial toxins, anti-neoplastic and immunosuppressive agents, thalidomide, aminoglycoside antibiotics (ototoxicity) and penicillin derivatives (seizures), cardioprotective agents (beta-blockers, digitalis derivatives and amiodarone).

As illustrated by the preceding list, compositions and methods of the invention can find use in the treatment of human neural injury and disease. Still more generally, the compositions and methods of the invention find use in the treatment of human patients suffering from neural damage as the result of acute brain injury, including but not limited to diffuse axonal injury, perinatal hypoxic-ischemic injury, traumatic brain injury, stroke, ischemic infarction, embolism, and hypertensive haemorrhage; exposure to CNS toxins, infections of the central nervous system, such as, bacterial meningitis; metabolic diseases such as those involving hypoxic-ischemic encephalopathy, peripheral neuropathy, and glycogen storage diseases; or from chronic neural injury or neurodegenerative disease, including but not limited to Multiple Sclerosis, Lewy Body Dementia, Alzheimer's disease, Parkinson's disease and Huntington's disease. Patient's suffering from such diseases or injuries may benefit greatly by a treatment protocol able to initiate neuronal proliferation and migration, as well as neurite outgrowth.

Still more generally, the invention has application in the induction of neuronal and neuroblast migration into areas of damage following insult in the form of trauma, toxin exposure, asphyxia or hypoxia-ischemia.

Uses of NRPs in Treating Obstetric Complications

Trophoblasts are essential in maintaining early pregnancy. They are among the first cells to differentiate to form the outer layer of the blastocyst, they secure its implantation in the uterine wall and subsequently develop into a placenta. The differentiation of trophoblasts following the implantation of the blastocyst results in the creation of extravillous trophoblast cells (EVT) that migrate and invade the uterine stroma. The trophoblast stem cells fuse to form syncytiotrophoblasts, which form anchoring villous trophoblasts. The villous trophoblasts give rise to a sub-population known as extravillous trophoblasts. Extravillous trophoblasts invade the uterine wall and its blood vessels and remodel the maternal spiral arteries by displacing smooth muscle and endothelial cells. As a result, blood vessels that are characterised by a larger diameter, an increased blood flow and a reduced resistance are produced. This step is essential for providing for the higher blood supply requirements of the fetus later in the pregnancy and, as a consequence, for maintaining a normal pregnancy.

Trophoblasts differentiate into endothelial-like cells in the spiral arteries of the endometrium where they remodel the arteries by replacing the smooth muscle and the endothelial cells to achieve a similar effect: an increase in vessel diameter, increase in blood flow and decrease in resistance zone.

In vitro studies suggest that in normal pregnancy, maternal cells may play a role in controlling the trophoblast invasion, although the exact nature of the regulatory interactions between these cells is unknown (Campbell et al., 2003). Deficient human trophoblast invasion into the maternal decidua appears to be a major feature of the pregnancy-associated pre-eclampsia. A failure to remodel the maternal spiral arteries, for example, is thought to restrict the blood flow to the developing foetus and contribute to the onset of pre-eclampsia or intrauterine growth restriction. The reasons for the failure are not known, but it is postulated that they may include an increase in the apoptosis of trophoblasts or compromised invasiveness of the trophoblasts.

Pre-eclampsia is characterized by a sudden onset of maternal hypertension, proteinuria and edema. In a pre-ecalmptic patient the cytotrophoblast invasion is shallow and vascular transformation is incomplete. Pre-eclampsia has been the leading cause of maternal mortality in the developed countries. Worldwide the disease is responsible for approximately 150,000 deaths per year. It also leads to considerable mortality and morbidity in newborn children and is expected to carry health implications in adult life, including increased risk of hypertension, heart disease and diabetes.

Intra-uterine growth restriction (IUGR), paired with permanent hypoxic placental conditions associated with the pathological condition of pre-eclampsia, lead to a retarded placental growth, putative birth complications and/or damages to the human foetus (e.g. a necessity for a pre-mature caesarean section resulting in a very low birth weight). A rare outcome of pre-eclampsia is a syndrome characterized by hepatic and renal failure with putative fatal outcome, so called "HELLP" syndrome (Haemolysis, Elevated Liver enzymes, Low Platelets) syndrome (Volz et al., 1992).

Patients with inherited thrombophilias developing pre-eclampsia during pregnancy have been shown to respond to a low molecular weight heparin treatment (LMWH-therapy) that can reverse some clinical symptoms (Saisto et al., 2004). Nevertheless, other forms of pre-eclampsia do not respond to LMWH-therapy.

It is therefore beneficial to establish a treatment or prophylaxis, which would increase the migration and invasiveness of trophoblasts during pregnancy in order to prevent the development of pre-eclampsia, HELLP syndrome or IUGR.

Administration of NRPs

NRP compounds, including NRP-1, its orthologs, analogs, paralogs, the NPRs disclosed herein and prodrugs containing the identified NRP peptide domains, can be used to promote neuronal and neuroblast migration. Most conveniently, this can be affected through direct administration of NRP compounds to the patient.

However, while NRPs can be advantageously used, there is no intention to exclude administration of other forms of NRP compounds. For example, human paralog forms or peptide fragments of NRP can be administered in place of NRP. By way of example, the effective amount of NRP in the CNS can be increased by administration of a pro-drug form of NRP that comprises NRP and a carrier, NRP and the carrier being joined by a linkage that is susceptible to cleavage or digestion within the patient. Any suitable linkage can be employed which will be cleaved or digested to release NRP following administration.

Another suitable treatment method is for NRP levels to be increased through an implant that is or includes a cell line that is capable of expressing NRP or analogs, paralogs or propeptides of an NRP in an active form within the central nervous system of the patient.

An NRP can be administered as part of a medicament or pharmaceutical preparation. This can involve combining NRP compounds with any pharmaceutically appropriate carrier, adjuvant or excipient. Additionally an NRP compound can be used with other non-NRP neuroprotective, proliferative, or other agent. The selection of the carrier, adjuvant or excipient will of course usually be dependent upon the route of administration to be employed.

The administration route can vary widely. An NRP may be administered in different ways: intraperitoneal, intravenous or intracerebroventricular. The peripheral application may be the way of choice because then there is no direct interference with the central nervous system.

Any peripheral route of administration known in the art can be employed. These can include parenteral routes for example injection into the peripheral circulation, subcutaneous, intraorbital, ophthalmic, intraspinal, intracisternal, topical, infusion (using eg. slow release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (eg. amounts which eliminate or reduce the patient's pathological condition) to provide therapy for the neurological diseases described above.

One route of administration includes subcutaneous injection (e.g., dissolved in 0.9% sodium chloride) and oral administration (e.g., in a capsule).

It will also be appreciated that it may on occasion be desirable to directly administer NRP compounds to the CNS of the patient by any appropriate route of administration. Examples include administration by lateral cerebroventricular injection or through a surgically inserted shunt into the lateral cerebral ventricle of the brain of the patient.

Therapeutic Doses of NRPs

In some embodiments of this invention, methods for treating brain damage comprise administering one or more NRPs in a dose range of from about 0.01 µg/kg body weight to about 100 µg/kg body weight. In other embodiments, a dose of 1 µg/kg body weight to about 10 µg/kg body weight can be useful. We have found that at a dose of about 4.16 µg/kg, mice with EAE showed significant improvement in motor function compared to control animals treated with saline only (see Example 3). In further embodiments, a dose of an NRP can be in the range of about 0.01 µg/kg body weight to about 0.1 mg/kg.

In other embodiments, the determination of an effective amount of an NRP to be administered is within the skill of one of ordinary skill in the art, and will be routine to those persons skilled in the art. In certain embodiments, the amount of an NRP to be used can be estimated by in vitro studies using an assay system as described herein. The final amount of an NRP to be administered will be dependent upon the route of administration, upon the NRP used and the nature of the neurological disorder or condition that is to be treated. A suitable dose range may for example, be between about 0.1 µg to about 15 µg per 1 kg of body weight or in other embodiments, about 20 µg/kg to about 30 µg/kg body weight per day.

For inclusion in a medicament, NRP can be directly synthesized by conventional methods such as the stepwise solid phase synthesis method of Merrifield et al., 1963 (J. Am. Chem. Soc. 15:2149-2154) or Goodman M. (ed.), "Synthesis of Peptides and Peptidomimetics" in Methods of organic chemistry (Houben-Weyl) (Workbench Edition, E22a,b,c,d, e; 2004; Georg Thieme Verlag, Stuttgart, New York), expressly incorporated herein fully by reference. Such methods of peptide synthesis are known in the art, and are described, for example, in Fields and Colowick, 1997, *Solid Phase Peptide Synthesis* (Methods in Enzymology, vol. 289), Academic Press, San Diego, Calif., expressly incorporated herein fully by reference. Alternatively synthesis can involve the use of commercially available peptide synthesizers such as the Applied Biosystems model 430A.

As a general proposition, the total pharmaceutically effective amount of an NRP administered parenterally per dose will be in a range that can be measured by a dose response curve. For example, an NRP in the blood can be measured in body fluids of the mammal to be treated to determine dosing. Alternatively, one can administer increasing amounts of an NRP compound to the patient and check the serum levels of the patient for the NRP. The amount of NRP to be employed can be calculated on a molar basis based on these serum levels of the NRP.

One method for determining appropriate dosing of the compound entails measuring NRP levels in a biological fluid such as a body or blood fluid. Measuring such levels can be done by any means, including RIA and ELISA. After measuring NRP levels, the fluid is contacted with the compound using single or multiple doses. After this contacting step, the NRP levels are re-measured in the fluid. If the fluid NRP levels have fallen by an amount sufficient to produce the desired efficacy for which the molecule is to be administered, then the dose of the molecule can be adjusted to produce maximal efficacy. This method can be carried out in vitro or in vivo. This method can be carried out in vivo, for example, after the fluid is extracted from a mammal and the NRP levels measured, the compound herein is administered to the mammal using single or multiple doses (that is, the contacting step is achieved by administration to a mammal) and then the NRP levels are remeasured from fluid extracted from the mammal.

NRP compounds are suitably administered by a sustained-release system. Suitable examples of sustained-release compositions include semi-permeable polymer matrices in the form of shaped articles, for example, films, or microcapsules. Sustained-release matrices include polylactides (U.S. Pat. No. 3,773,919, EP 58,481), poly(2-hydroxyethyl methacrylate) (Langer et al., 1981), ethylene vinyl acetate (Langer et al., supra), or poly-D-(–)-3-hydroxybutyric acid (EP 133, 988). Sustained-release compositions also include a liposomally associated compound. Liposomes containing the compound are prepared by methods known to those of skill in the art, as exemplified by DE 3,218,121; Hwang et al., 1980; EP 52,322; EP 36,676; EP 88,046; EP 143,949; EP 142,641; Japanese Pat. Appln. 83-118008, U.S. Pat. Nos. 4,485,045 and 4,544,545 and EP 102,324. In some embodiments, liposomes are of the small (from or about 200 to 800 Angstroms) unilamellar type in which the lipid content is greater than about 30 mol. percent cholesterol, the selected proportion being adjusted for the most efficacious therapy. All U.S. parents referred to herein, both supra and infra, are hereby expressly incorporated by reference in their entirety.

PEGylated peptides having a longer life than non-PEGylated peptides can also be employed, based on, for example, the conjugate technology described in WO 95/32003 published Nov. 30, 1995.

In some embodiments, the compound can be formulated generally by mixing each at a desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. It can be appreciated that the above doses are not intended to be limiting. Other doses outside the above ranges can be determined by those with skill in the art.

In some embodiments, formulations can be prepared by contacting a compound uniformly and intimately with liquid carriers or finely divided solid carriers or both. Then, if desired, the product can be shaped into the desired formulation. In some embodiments, the carrier is a parenteral carrier, alternatively, a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are desirably non-toxic to recipients at the dosages and concentrations employed, and include, by way of example only, buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, and the like. In certain embodiments, a peptide of this invention can be stabilized using 0.5 M sucrose or 0.5 M trehalose. Using such sugars can permit long-term storage of the peptides.

An NRP compound can be desirably formulated in such vehicles at a pH of from about 6.5 to about 8. Alternatively, the pH can be from about 4.5 to about 8. It will be understood that use of certain of the foregoing excipients, carriers, or stabilizers will result in the formation of salts of the compound. The final preparation may be a stable liquid or lyophilized solid.

In other embodiments, adjuvants can be used. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

Desirably, an NRP compound to be used for therapeutic administration may be sterile. Sterility can be readily accomplished by filtration through sterile filtration membranes (e.g., membranes having pore size of about 0.2 micron). Therapeutic compositions generally can be placed into a container having a sterile access port, for example an intravenous solution bag or vial having a stopper pierceable by a hypodermic injection needle.

In other embodiments, an NRP compound can be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 0.01% (w/v) aqueous solution of compound, and the resulting mixture is lyophilized. The infusion solution can be prepared by reconstituting lyophilized compounds using bacteriostatic water or other suitable solvent.

In still further embodiments, a kit may contain a predetermined amount of lyophilized NRP, a physiologically compatible solution for preparation of a dosage form, a mixing vial, a mixing device, and instructions for use. Such kits can be manufactured and stored according to usual practices in the industry.

An NRP-containing composition may be administered by one or more of a variety of routes. By way of example, intravenous, intraperitoneal, intracerebral, intraventricular, inhalation, lavage, rectal, vaginal, transdermal, subcutaneous administration can be used.

Gene Therapy

In other embodiments of this invention, therapeutic methods include gene therapy for treating an organism, using a nucleic acid encoding an NRP compound. Generally, gene therapy can be used to increase (or over-express) NRP levels in the organism. Examples of nucleotide sequences include those that encode peptides depicted in SEQ ID NOs: 1-5 and 7-20. Such nucleotide sequences can be readily appreciated by reference to the genetic code. Because the peptides of this invention are relatively short, any nucleotide sequence having an open reading frame appropriate to NRPs of this invention can be used, not only the native sequence based on mRNAs for the NRPs. It can be appreciated that oligonucleotides complementary to reading strand sequences can be used.

Thus, complementary single stranded and double stranded oligonucleotides that can be incorporated into larger oligonucleotides can be used. For example, inserting a cassette containing an open reading frame for an NRP can be accomplished using methods well known in the art and need not be described in detail here. However, such methods include those described in Sambrook and Russell, *Molecular Cloning: A Laboratory Manual*, Third Edition (2001), expressly incorporated herein fully by reference, and other standard reference materials. It can be appreciated that additional sequences can be used to encode a pro-NRP peptide, which, upon cleavage, can result in a biologically active NRP.

Any suitable approach for transfecting an organism with a sequence encoding an NRP can be used. For example, in vivo and ex vivo methods can be used. For in vivo delivery, a nucleic acid, either alone or in conjunction with a vector, liposome, precipitate etc. can be injected directly into the organism, for example, a human patient, and in some embodiments, at the site where the expression of an NRP compound is desired. For ex vivo treatment, an organism's cells are removed, the nucleic acid is introduced into these cells, and the modified cells are administered to the organism either directly or, for example, encapsulated within porous membranes which are implanted into the patient. See, e.g. U.S. Pat. Nos. 4,892,538 and 5,283,187, expressly incorporated herein fully by reference.

We have demonstrated herein that cultured cells can express NPRs, and that when those NRP-expressing cells are incubated with neurons susceptible to toxic damage, NPRs can be expressed, secreted into the medium and can protect the neurons from toxic damage. This surprising finding supports a therapeutic approach to treating neural degeneration by gene transfer and subsequent NRP-recombinant cell transplantation.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a RNA retrovirus. In certain embodiments, in vivo nucleic acid transfer techniques include transfection with viral vectors (such as adenovirus, Herpes simplex I virus, or adeno-associated virus) and lipid-based systems (useful lipids for lipid-mediated transfer of the gene are N-[1-(2,3-dioleyloxy)propyl]-N,N,N-trimethylammonium (DOTMA), dioleoylphatidylethanolamine (DOPE) and 3-β[N—(N',N'-dimethylaminoethane)carbomoyl]cholesterol (DC-Chol), for example. In some situations it may be desirable to provide the nucleic acid source with an agent that directs the nucleic acid-containing vector to target cells. Examples of "targeting" molecules include antibodies specific for a cell-surface membrane protein or the target cell, a ligand for a receptor on the target cell, a fusion between bacterial Penetratin™ and the nucleotide and/or peptide sequence to target the plasma membrane, to be used for proper post-translational processing and other known cellular processes required to synthesize functional proteins and peptides. Penetratin™ 1 is a patented 16-amino acid peptide corresponding to the third helix of the homeodomain of Antennapedia protein. This peptide is able to translocate across biological membranes by an energy-independent mechanism and has been used successfully to internalize covalently attached peptides and oligonucleotides and to convey them to the cytoplasm and nucleus of many cell types. Activated Penetratin™ 1 couples to oligos and peptides that carry a thiol (—SH) function. Activated Penetratin™ 1 is also available biotinylated to permit detection using suitable avidin or streptavidin reagents.

In embodiments where liposomes are employed, proteins that bind to a cell-surface membrane protein associated with endocytosis may be used for targeting and/or to facilitate uptake. Examples of such proteins include capsid proteins and fragments thereof tropic for a particular cell type, antibodies for proteins, which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. The above articles and applications are expressly incorporated herein fully by reference.

Kits are also contemplated within the scope of this invention. A typical kit can comprise a container, in some embodiments a vial, for the NRP formulation comprising one or more NRP compounds in a pharmaceutically acceptable buffer and instructions, such as a product insert or label, directing the user to utilize the pharmaceutical formulation.

EXAMPLES

The following examples are provided to illustrate certain embodiments of this invention. It can be readily appreciated that other embodiments can be devised and still remain within the scope of this invention. All of these other embodiments are considered to be part of this invention.

Example 1

Effects of NRPs on Survival and Proliferation of Cerebellar Microexplants NRP Preparation NRP-5 RG analogue D6A (SEQ ID NO: 1) and NRP-5GG analogue D4A (SEQ ID NO: 2) were ordered from Auspep (Australia). The peptides were synthesized using standard solid-phase synthesis. The peptides were supplied with an amidated C-terminus, and were more than 95% pure as analyzed by MALDI-MS spectrum analysis. The peptides were stored lyophilized at −80° C. under argon in 0.5M sucrose or 0.5M trehalose until usage. They were reconstituted in PBS, alternatively in 100 µg/ml human transferrin/PBS or in other embodiments in 100 µg/ml BSA/PBS, in 0.5M sucrose or 0.5M trehalose.

Cell Culture Preparation

Laminated cerebellar cortices of the two hemispheres were explanted from a P3, P4, P7 or P8 Wistar rat, cut into small pieces in GBSS with 0.65% D(+)glucose solution, and triturated by a 0.4 mm gauge needle and subsequently pressed through a 125 µm pore size sieve. The obtained microexplants were centrifuged (60×g) 2 times for a medium exchange into serum-free BSA-supplemented START V-medium (Biochrom). Finally, the microexplants were reconstituted in 500 µl STARTV-medium. For culturing, 38 µl of the cell suspension was incubated for 1 hour on a poly-D-lysine-coated cover slip in a 35 mm Petri dish under an atmosphere comprising 5% $CO_2$ in air and 100% humidity at 34° C. Subsequently, the injuring toxins (as described below), NRPs and 1 ml of STARTV-medium were added, and the cultures were evaluated after 2-3 days of culture.

For immunohistochemistry and neuronal migration experiments, cerebellar microexplants were fixed after 2-3 days in culture after the following regime: microexplants were fixed by 2-minute, serial treatment with 0.4%; 1.2%; 3% paraformaldehyde, respectively, followed by a 5 min incubation in 4% paraformaldehyde/0.25% glutaraldehyde in 0.1 M sodium phosphate (pH 7.4).

Effects of NRPs on Toxin-Induced Neural Injury

Toxicological and drug administration experiments were designed such that ¹/₁₀₀ parts of toxin and neuroprotective drug were administered simultaneously to the freshly prepared cerebellar microexplants. Glutamate was prepared as a 50 mM stock solution in MilliQ water while 50 mM 3-nitropropionic acid was pH-adjusted (pH 6.8-7.2) in MilliQ water. The concentrations of the oxidative stress inducing toxin, 3-nitropropionic acid (3-NP), and the excitotoxin, glutamate, in the assay were 0.5 mM each. Lyophilized peptides were reconstituted in PBS or 100 µg/ml human transferrin as a 10 µM stock solution. Subsequently, serial dilutions were made. Cerebellar microexplants were cultivated for 48-72 hours at 34° C., 5% $CO_2$ in air and 100% humidity before they were fixed by increasing amounts of paraformaldehyde (0.4%, 1.2%, 3% and 4%—each treatment 2-3 min).

Using the toxins described above, cerebellar explants were exposed for 24 hours, at the beginning of culturing to dilutions of NRP (survival assay) or NRP and 0.1 µM BrdU (proliferation assay). Subsequently, 80% of the medium was changed without addition of new toxins and NRPs. The cerebellar cultures were fixed as described above after 3 days in vitro. The detection of the incorporated BrdU level was performed as described previously.

Data Reduction and Statistical Analysis

For statistical analysis of survival, four fields (each field having an area of 0.65 $mm^2$) of each fixed cerebellar culture with the highest cell densities were chosen, and cells displaying neurite outgrowth were counted (survival assay).

For statistical analysis of proliferation BrdU-positive nuclei were counted. Statistical significance was measured by Student's t-test.

Results

Neuroprotection

NRP-5 segment RG analogue D6A (SEQ ID NO: 1; 100 fM concentration), conferred survival rates of 39.1% neuroprotection when simultaneously administered with the toxins after severe injury (FIG. 1). Neuroprotectants like IGF-1 only achieve rescue values of approximately 20% protection in this particular assay. The high potency of NRPs is notable.

Neuronal Proliferation

Figure 2:
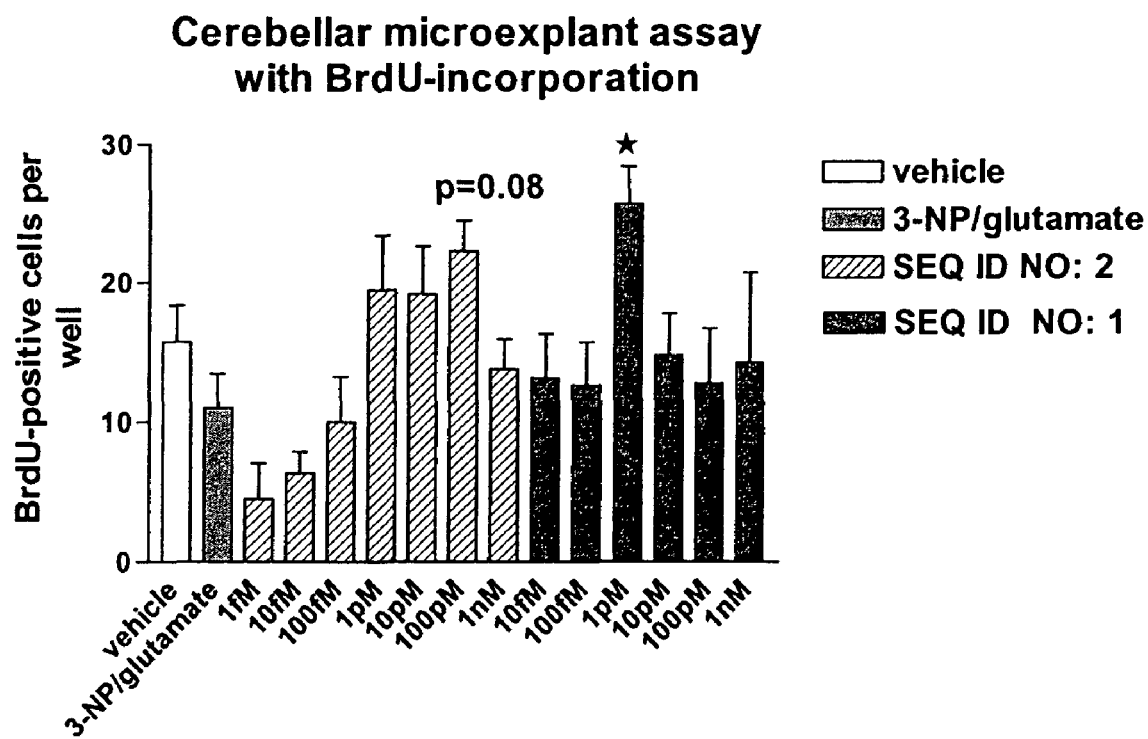
FIG. 2 depicts the proliferation-inducing capacity of NRP-5 segment GG analogue D4A (SEQ ID NO: 2) and NRP-5 segment RG analogue D6A (SEQ ID NO: 1) within cerebellar cells. Student's t-test was used for statistical analysis (* $p<0.02$, N=8).

NRP-5 RG analogue D6A (SEQ ID NO: 1; 1 pM) increased the proliferation rate in these cultures significantly compared to the uninjured vehicle (FIG. 2). NRP-5 GG analogue D4A (SEQ ID NO: 2; 100 pM) had a similar effect to increase proliferation. Both compounds are highly proliferation-inducing ($p<0.01$) when compared against injured cells without NRP (FIG. 2). We conclude that NRP-5 RG analogue D6A and NRP-5 GG analogue D4A each induced neuronal proliferation and that these NRPs can be useful to treat neurodegeneration associated with neural injury or disease.

Example 2

NRP-Mediated Migration in Physiological (Injury-Free) Conditions

An NRP was tested for migration-inducing/chemoattractive activity on mouse neural stem cells in a haptotactic migration assay as described below.

Methods

Initial NRP Coating

Control wells of Transwell plates (Corning) with 12 µm pore size were coated in 1.5 ml of the BSA/PBS vehicle. Remaining plates were coated using 0.1 ng/ml of NRP (SEQ ID NO: 1) (prepared in PBS containing 10 ug/ml BSA).

Extracellular Matrix Coating

Laminin (7 µg/ml) was used as extracellular matrix (ECM) coating for mouse primary stem cells. The matrix was incubated at 37° C.; 5% $CO_2$ for 2 hrs at room temperature. The cells were seeded onto the inserts (30,000 cells per well). Plates were fixed at 1-2 days in vitro (DIV).

Coating of Inserts

A 5 ug/mL PDL/PLL mixture (in PBS) was used to coat inserts. Subsequently the inserts were rinsed with MilliQ water.

Cell Fixation

Inserts were discarded and wells fixed in successive dilutions of PFA (0.4, 1.2, 3 and 4%) for 3-5 min in each dilution. The wells were rinsed and stored in successive dilutions of PFA (0.4, 1.2, 3 and 4%) 3-5 min in each dilution. The wells were rinsed and stored in PBS until counting. All cells that displayed neurite outgrowth and traveled to the bottom chamber were counted as migrating cells.

Results

Figure 3A:
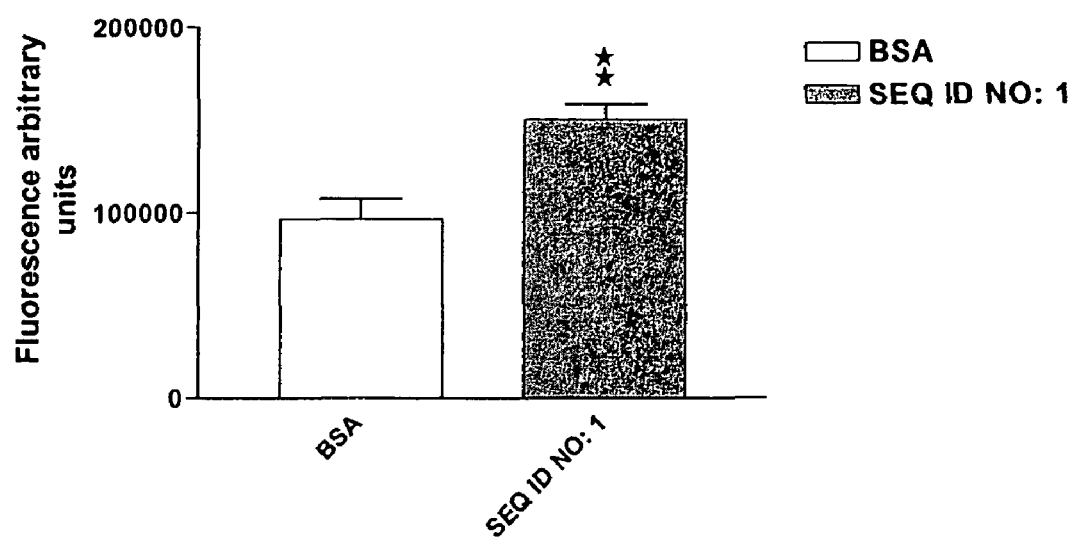
FIGS. 3A and 3B depict graphs of results of studies of neuronal migration induction by NRPs.

55% more cells migrated in plates treated with NRP than migrated in plates without NRP. The NRP-5 RG analogue D6A (SEQ ID NO:1; 0.1 ng/ml) caused 55.4% more MEB-5 cells to migrate to the bottom of the culture dish in comparison with the BSA-vehicle alone (FIG. 3A). We conclude that NRP-5 RG analogue D6A induced neuronal cell migration, and that they each can be used to treat neurodegeneration associated with neural injury or disease.

Example 3

NRP-Mediated Migration in Injury Conditions

The NRP of SEQ ID NO: 1 was tested for migration-inducing/chemoattractive activity on mouse neural stem cells in a haptotactic migration assay in injury conditions, as described below.

Methods

Production of a Monolayer of Astrocytes

P1 (postnatal day 1) Wistar or Sprague Dawley rats were sacrificed by decapitation. Cortical hemispheres were removed and collected into separate tubes containing 4 ml DMEM—1 cortex per tube. The tissue was mechanically triturated. Cells were transferred into medium using a sterile pipette and filtered through a 100 um cell strainer into a 50 ml centrifuge tube. Each tube was stocked up to 50 ml with DMEM. The tubes were centrifuged for 5 mins at 350×g at 22° C. The cells were resuspended in 40 ml of DMEM+10% FBS. The cells were then seeded into a 12-well plate+5 nM ocadaic acid (to remove neurons by inducing apoptotic cell death) and incubated at 37° C./10% $CO_2$ for 24 hrs in a Boyden Chamber. The medium+FBS was replaced after 1 day with fresh DMEM+10% FBS. The cell growth was monitored until confluency (14-18 days).

Pharmacological and Mechanical Injury

Induction of injuries to the astrocytic monolayer was accomplished using the pharmacological agent transforming growth factor β1 (TGFβ1) and simultaneous mechanical scratching of the monolayer in order to activate astrocytics. 10 ng/ml TGFβ1 was administered to the astrocytic monolayer for 24 hrs. Additionally, astrocytic cultures were mechanically injured by a scalpel (one scratch throughout the bottom of the well).

Seeding of Pre-Labelled Stem Cells

Undifferentiated fluorescein diacetate-labelled embryonic mouse neural stem cells (NSCs) were seeded into Poly-D-Lysine (PDL—5 μg/ml) coated inserts. The lower compartment of the Boyden chamber received 100 fM NRP-5 RG analogue D6A (SEQ ID NO:1).

Cell Fixation

Inserts were discarded and wells fixed in successive dilutions of PFA (0.4, 1.2, 3 and 4%) for 3-5 min in each dilution. The wells were rinsed and stored in successive dilutions of PFA (0.4, 1.2, 3 and 4%) 3-5 min in each dilution. The wells were rinsed and stored in PBS until counting. All cells that displayed neurite outgrowth and traveled to the bottom chamber were counted as migrating cells.

Analysis

Migrated stem cell number of labelled cells were analysed after 24 hrs by a fluorescence-based computerized imaging system (Discovery-1).

Results

Figure 3B:
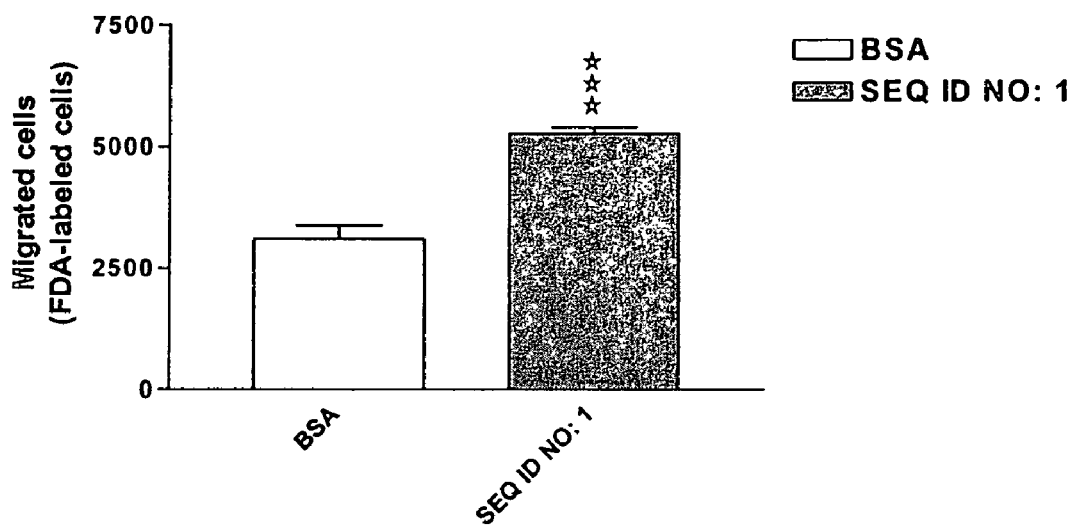

NRP-5 RG analogue D6A (SEQ ID NO: 1; 100 fM) 69.1% stimulated more stem cells to migrate than vehicle-treated controls (FIG. 3B). We conclude that NRP-5 RG analogue D6A induced neuronal stem cell migration, and that this NRP can be useful to treat neurodegeneration associated with neural injury or disease.

Example 4

Therapeutic and Prophylactic Effects of NRPs in a Model of Multiple Sclerosis

Therapeutic and prophylactic effects of NRPs were studied in experimental autoimmune encephalomyelitis (EAE) induced by myelin oligodendrocyte glycoprotein (MOG), a recognized animal model for Multiple Sclerosis (MS).

Methods and Materials

Animals

Female mice, 6-8 weeks-old, strain C57Bl/6J weighing an average of 24 g each were used.

NRP Preparation

NRP-5 segment RG (SEQ ID NO:3) was supplied by Auspep (Australia). It was supplied with an amidated C-terminus, and was more than 95% pure as determined by HPLC. The sequence was confirmed by mass spectroscopy. The peptide was stored lyophilized at a temperature of −80° C. under argon gas until use. The peptide was reconstituted in PBS on the day of use. Other NRPs were provided as above.

The following NRPs were used:

A 13-mer NRP-5 segment RG (also known as SEQ ID NO: 30 disclosed in U.S. patent application Ser. No. 10/976,699) is

REGRRDAPGRAGG          SEQ ID NO: 3

A 25-mer NRP-4 GG, also known as (SEQ ID NO: 29 disclosed in U.S. patent application Ser. No. 10/976,699) is

GTPGRAEAGGQVSPCLAASCSQAYG.     SEQ ID NO: 4

A 24-mer NRP-7 SW, also known as SEQ ID NO: 24 disclosed in U.S. patent application Ser. No. 10/976,699 is

SEPEARRAPGRKGGVVCASLAADW.      SEQ ID NO: 5

Induction EAE

A 200 μL of an emulsion containing 200 μg of the encephalitogenic peptide MOG35-55

MEVGWYRSPFSRVVHLYRNGK          SEQ ID NO: 6 was obtained from C S Bio Co. USA) in complete Freund adjuvant (Difco, Detroit, USA) containing 800 μg Mycobacterium tuberculosis (Difco, Detroit, USA) was injected subcutaneously into one flank. Mice were immediately injected intraperitoneally with 400 ng pertussis toxin (List Biological Laboratories, USA) and again 48 hours later.

Treatment

Therapeutic

At the peak of the disease (day 17 after MOG-immunization) animals were treated with NRP-5RG (SEQ ID NO: 3) intraperitoneally (i.p.) for 14 days with a daily dose of 0.1 μg peptide/animal (4.16 μg/kg).

Prophylactic

Mice were injected with the drug intraperitoneally for 14 consecutive days commencing on day 5 after the encephalitogenic challenge with MOG35-55. The dose of NRP-4 GG (SEQ ID NO: 4) was 1 ug peptide/day and the dose of NRP-7 SW (SEQ ID NO: 5) was 0.2 μg peptide/day (8.33 μg/kg).

Assessment of Neurological Impairment

Mice were monitored daily and neurological impairment was scored on an arbitrary clinical score as follows: 0, no clinical sign; 1, flaccid tail; 2, hind limb weakness; 3, hind limb paralysis; 4, hind limb weakness and fore limb weakness; 5, paraplegia; 6, death.

Results

Therapeutic Effects of NRPs on EAE in Mice

Figure 4:
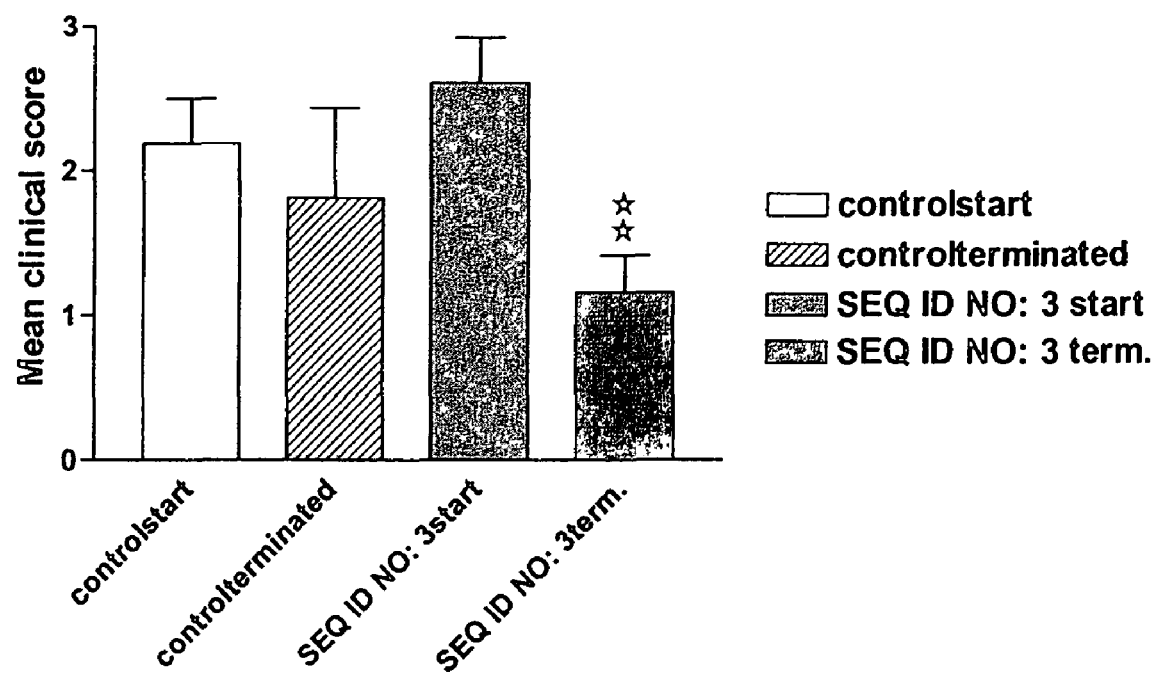
FIG. 4 shows significant long-term potential of NRP-5 segment RG (SEQ ID NO: 3) to decrease the severity of motoric impairment occurring within MS disease model of EAE when administered as therapeutic drug at the peak of the disease. Score 1 is the lowest score and implies a flaccid tail only while the higher scores imply weakness (score 2) or complete paralysis of the hind legs (score 3). Kruskal-Wallis-test was used for statistical analysis (✿ ✿  $p=0.01$, N=9).

NRP treatment administered daily i.p. for 14 consecutive days starting at the peak of the disease resulted in a drop of the treated group from a mean clinical score of 2.61 to 1.16. The effect observed in the control group was insignificant (FIG. 4).

Prophylactic

In animals with EAE, disease typically develops from 10 days following the immunization with MOG. Intraperitoneal injection started on day 5 after immunization with MOG and continued until day 18.

Figure 5B:
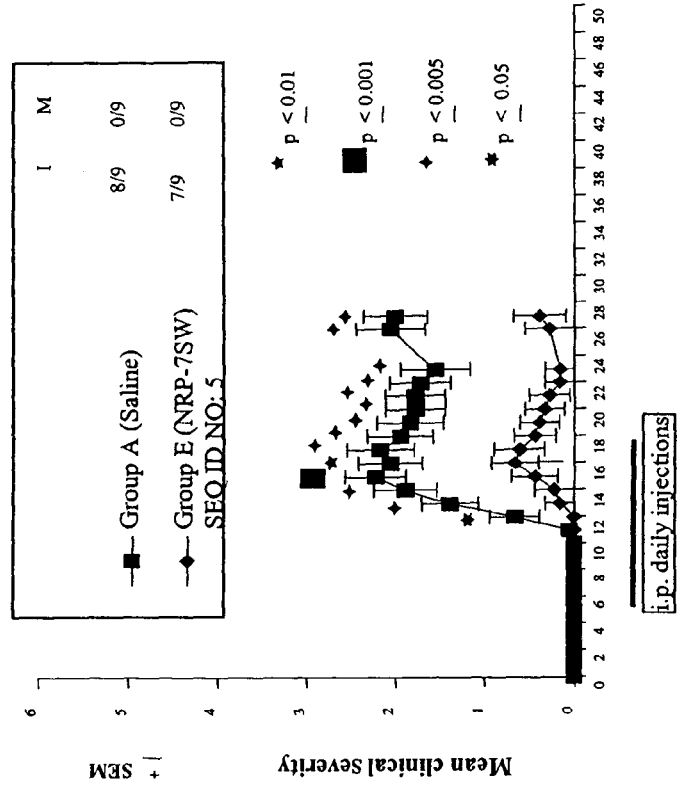
FIG. 5B depicts the efficacy of NRP-7SW (SEQ ID NO: 5) in ameliorating adverse effects of experimental allergic encephalitis (EAE) in an animal model.
Figure 5A:
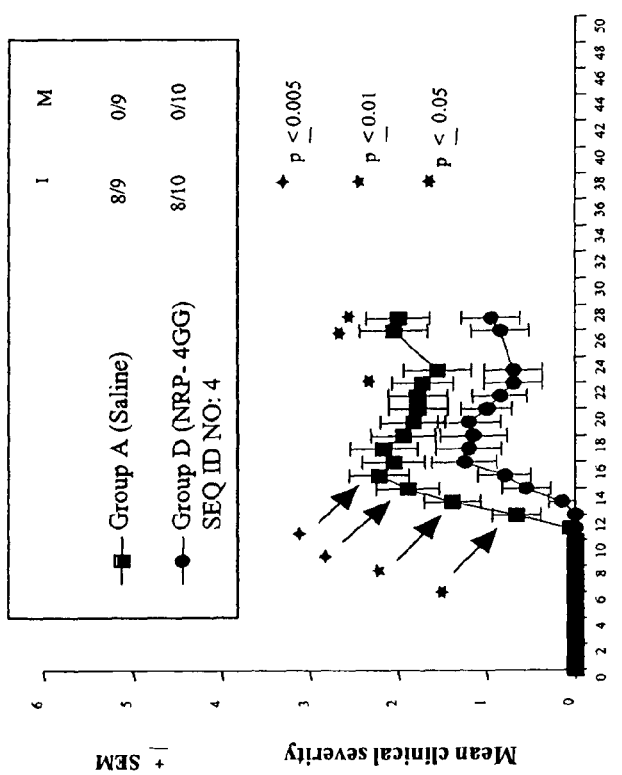
FIG. 5A shows the efficacy of NRP-4GG (SEQ ID No: 4) in ameliorating adverse effects of experimental allergic encephalitis (EAE) in an animal model.

FIG. 5 depicts results of studies comparing the effects of two NRPs of this invention on EAE in mice. FIG. 5A depicts a graph showing the efficacy of NRP-4GG (SEQ ID NO: 4) in attenuating development of motor symptoms of EAE following immunization with MOG. I stands for induction of disease, M stands for mortality. In the control group, 8 of 9 animals developed clinical symptoms of disease, as reflected in the increased clinical score. In the NRP-treated group, the incidence of disease was 8 out of 10. The mortality in both groups was 0.

FIG. 5B depicts results showing the efficacy of NRP-7SW (SEQ ID NO: 5) in attenuating the development of motor symptoms of EAE following immunization with MOG. The incidence of disease in the control group was 8 out of 9, and in the NRP-treated group was 7 out of 9. No animals died as a result of development of EAE.

From 12 days onwards, the animals treated with NRP-4RG exhibited significant attenuation of the disease profile (e.g., recovery of motor deficits) compared to the control group treated with saline only. The significant improvement lasted until day 27, the last day of the study. The average clinical score of the control group on day 27 was 2.0 and that of the NRP-treated group was 1.0 (FIG. 5A). In the group treated with mouse NRP-7SW, significant attenuation in clinical score was observed from day 12 onwards compared to control animals injected with saline alone. The averages for the control and NRP-treated groups were 2.0 and less than 0.5, respectively.

We conclude that NRPs can be useful in treating motor deficits associated with autoimmune disorders of the brain, and can be useful in treating multiple sclerosis in human beings.

Example 5

Effects of NRPs in Peripheral Neuropathy

Peripheral neuropathy in humans can be initiated by extremely high intake dosages of vitamin B6 (pyridoxine); oral doses up to 6 g for 12-40 months lead to a progressive sensory neuropathy manifested by sensory ataxia, diminished distal limb proprioception, paresthesia and hyperesthesia (Dalton and Dalton, 1987; Foca, 1985; Schaumburg and Spencer, 1979). Parry and Bredesen (1985) subsequently reported that as little as 200 mg of pyridoxine per day could induce the syndrome while the recommended daily intake dosage is 2-4 mg in human adults. Similar effects can be seen in experimental animals exposed to high doses of pyridoxine. Therefore, studies of pyridoxine-induced peripheral neuropathy in rats are directly applicable to effects observed in humans. In particular, therapeutic efficacy of NRPs in animal systems reasonably predict effects observed in human beings.

Therefore, we studied the effects of the NRPs on rats with experimental peripheral neuropathy induced by pyridoxine, a recognized model of the human disorder. In rat studies, an intraperitoneal dosing regime of 600-700 mg pyridoxine/kg/day for 8 to 15 subsequent days has been used and described in the art to mimic an intermediate pyridoxine dosage to inflict neuropathy pathology (Krinke et al., 1985; Xu et al., 1989 and Callizot et al., 2001).

Methods and Materials

All studies conducted using this animal system of peripheral neuropathy were carried out according to a protocol approved by the Animal Ethics Committee of the University of Auckland. The dosage regime and motor impairment analysis were conducted according to Callizot et al., 2001.

Animals

Adult male Sprague Dawley P50 rats were divided into the vehicle (n=9) and NRP-treated (n=10) groups. The rats were killed with an overdose of sodium pentobarbiturate on the 24 day from the first administration of pyridoxine.

Peripheral Neuropathy Induction

From day 1, all rats were injected intraperitoneally (IP), twice daily, with 350 mg/kg pyridoxine for 8 consecutive days. Pyridoxine (Sigma) solution for injections was made using the following proportions: 95 mg of pyridoxine and 41 mg sodium bicarbonate in 1 ml of water.

Drug Treatment

On days 1 to 10 the vehicle group (n=10) received one daily IP-injection of 24 mM sucrose and the rats in the NRP-treated group (n=10) received 4 µg/kg of NRP-5 segment GG analogue D4A (GRRAAPGRAGG-NH$_2$; SEQ ID NO:2) diluted in 24 mM sucrose. Lyophilised NRP was stored in the presence of sucrose or alternatively in trehalose at room temperature. For every intraperitoneal (i.p.) injection, NRP-5 segment GG analogue D4A was reconstituted to 100 µM peptide concentration containing 0.5M sucrose/trehalose, further diluted with PBS to the actual working solution of 5 µg/ml NRP-5 segment GG analogue D4A (containing 24 mM sucrose). A rat with a body weight of 250 g was injected with 200 µl of the working solution.

Analysis of Weight Loss after Pyridoxine Treatment

Animals are weighed daily during the experimental timeframe of 24 days. According to the study protocol, animals showing weight loss of more than 15% body weight were immediately killed. One of the control animals was sacrificed on day 4 of the pyridoxine treatment (control n=9).

Analysis of Motor Impairment after Pyridoxine Treatment

Overall motor impairment was analysed by assessing the gait of each rat: 1) on a flat surface and 2) its ability to walk across a wooden beam. The tests were carried out on days 8, 10, 13, 15, 17, 20 and 24 after the pyridoxine injection.

Physical Behaviour of the Animal when Placed on a Flat Surface

If the animal walked with no difficulty whatsoever, it was scored as a "0." If there appeared to be problems in its gait, it was placed on a raised wooden beam. If it balanced with difficulty when placed on the beam, score of "1" was given. If it clearly struggled to walk on a flat surface with hind limbs splayed out instead of tucked under its belly, it was scored as "2." When the rat displayed severe weakness, immobility or lay in lateral recumbency, it was given a score of "3." Two-way ANOVA with subsequent Bonferroni post test were used for statistical analysis.

Hind Limb Adduction Test

Overall motor movement impairment was analysed by assessing the ability of each rat to adduct (i.e. keep its limbs close to the body) its hind limbs. Pyridoxine intoxication results in the animal being unaware of the position of its legs. During the test, each rat was held in a vertical position above a flat surface and slowly lowered so that the foot pads of its hind limbs touched the surface. Normal rats will kick downwards in an attempt to maintain contact with a surface with both hind limbs before immediately drawing both of them back to the body (adduction). These were scored as "0". Rats that drew their hind limbs back after a slight delay were scored as "1". Rats that only drew a single limb back to the body after surface contact or respond in an intermittent fashion (unilateral adduction) were scored as "2" and finally rats that failed to draw their hind limbs back were scored as "3". Tests were carried out on days 8, 10, 13, 15, 17, 20 and 24.

Beam Walk Assessment

The precision beam walk test was used to assess the animals' precise coordinated movement on days 13, 17 and 24. Briefly, animals were habituated once daily for 7 days before start of pyridoxine treatment on a 1.5 m long beam (with two longitudinal stripes indicating the median of the beam). On day 0 (one day before pyridoxine/NRP treatment) a baseline of motor behaviour on the beam was videotaped. On day 13, 17 and 24 the animals were subjected to a 7-step walk on the beam and scored for every step according to the following grades: score 1—feet placed above the median line; score 2—feet placed on the superior part of the line; score 3—feet placed on the inferior part of the line; score 4—feet placed below the line. All scores were added for the 7-step walk to receive a total score for one tested animal at a given time point. If the tested rat could only stand on the beam but was unable to not walk it was given the score of 30, and if it was unable to stand on the beam, it was scored as 32.

Results

Weight Loss

Figure 6:
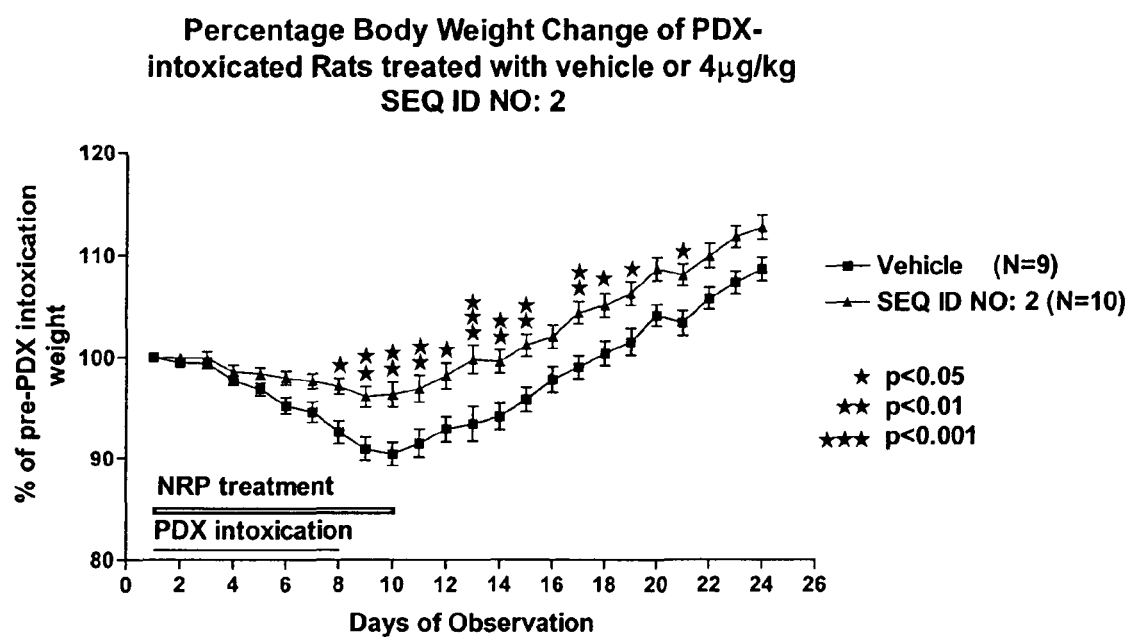
FIG. 6 shows the average body weight of the vehicle treated (n=9) and the NRP-treated groups (n=10) over the experimental time frame following pyridoxine injury. Two-way ANOVA test was used for statistical analysis of the data (☆ p<0.05; ☆☆ p<0.01; ☆☆☆ p<0.001).

From day 8 (end of pyridoxine treatment) until day 21 the body weight of the NRP-treated animals (NRP-5GG analogue D4A; GRRAAPGRAGG-NH$_2$; SEQ ID NO: 2) was significantly higher than that of the vehicle-treated group (FIG. 6). The NRP-treated animals (96.3+1.2% of day 1 weight) did not loose as much weight as the vehicle group (90.4+1.2% of day 1 weight) at the peak of weight loss at day 10 as a result of the pyridoxine treatment. The recovery from the initial 3.7% weight loss was much quicker in NRP-treated group than in control animals. After day 21 there was a trend in the NRP-treated group to gain more weight than the vehicle group.

Motor Impairment

Figure 7:
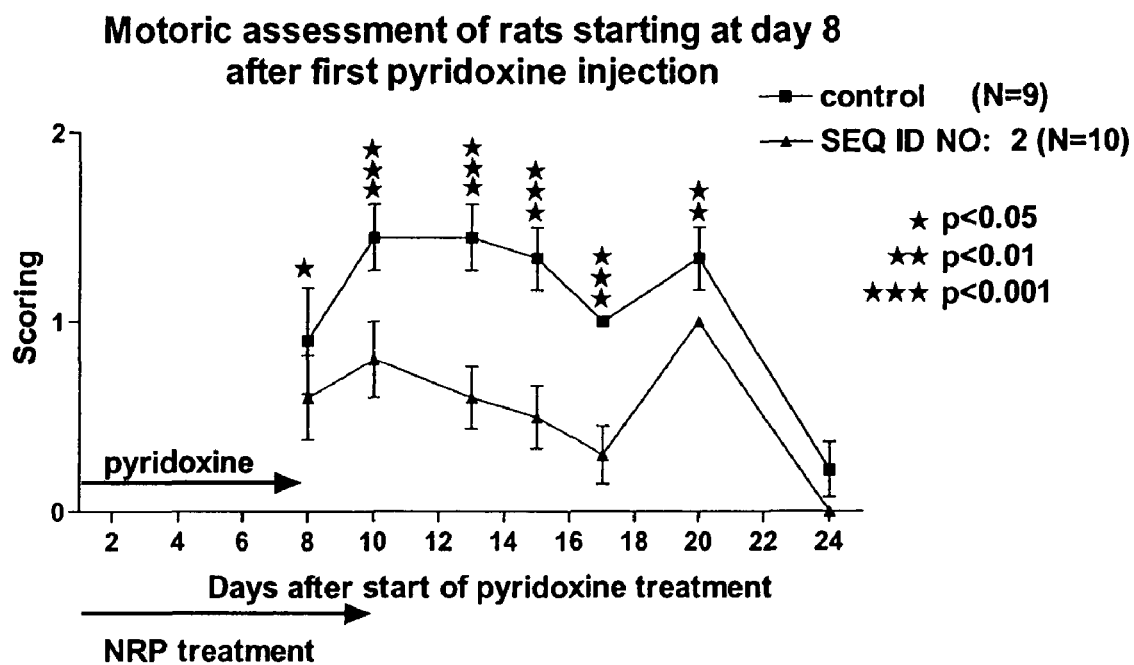
FIG. 7 shows the result of the motor assessment tests performed on days 8, 10, 13, 15, 17, 20 and 24 of the study, post-pyridoxine treatment. Two-way ANOVA with Bonferroni posttest were used for statistical analysis of the data (☆ p<0.05; ☆☆ p<0.01; ☆☆☆ p<0.001).

A highly significant attenuation of the motor impairment scores within the NRP-treated group was observed. At the peak of disease at day 13, the NRP-treated (NRP-5GG analogue D4A; SEQ ID NO: 2) showed no evident difficulty or only slight weakness throughout the experiment (score: 0.60+ 0.52), while all animals in the control group were impaired (score: 1.44+0.53). On day 24 all animals of the NRP-treated group had recovered (FIG. 7).

Hind Limb Adduction

Figure 8:
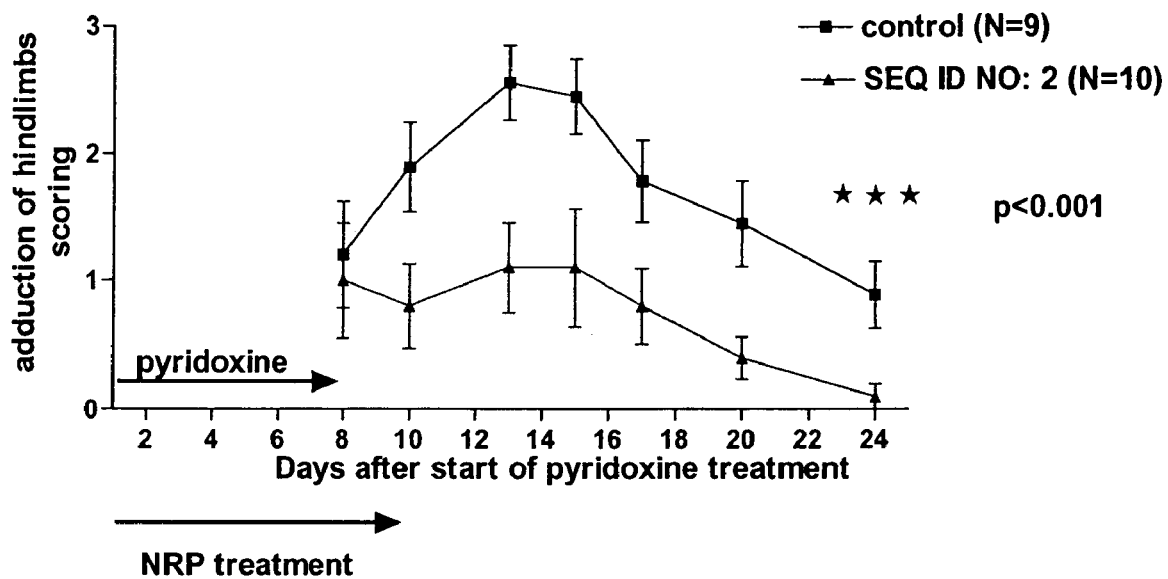
FIG. 8 shows the results of the hind limb adduction behaviour tests performed on days 8, 10, 13, 15, 17, 20 and 24 of the study, post-pyridoxine treatment. Two-way ANOVA test was used for statistical analysis of the data (☆☆☆ p<0.001).

The vehicle-treated animals showed a delayed or immediate adduction of hind limbs at the peak of the disease, between days 13-15 (FIG. 8). Animals treated with NRP-5GG analogue D4A (SEQ ID NO: 2) showed no or only intermittent adduction behaviour. At the end of the study 9 out of 10 animals from the NRP-treated group (score: 0.10+0.31) showed no sign of hind limb adduction after manual manipulation, while the control group still displayed signs of intermittent adduction (score: 0.88+0.78). The difference between both groups in the hind limb adduction test scores was highly significant. Significance analysed with Two-way ANOVA.

Beam Walking

Figure 9:
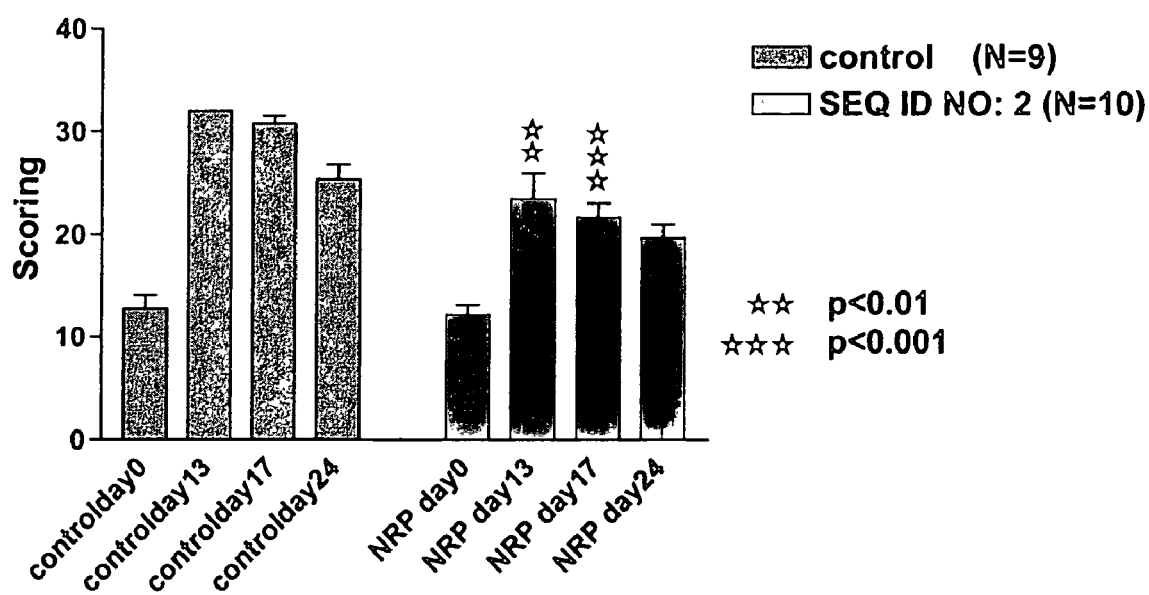
FIG. 9 shows the precision beam walk test conducted on day 0, 13, 17 and 24 of the study. Two-way ANOVA test followed by Bonferroni posttest were used for statistical analysis (☆☆ p<0.01; ☆☆☆ p<001).

On day 13 none of the animals in the control group was unable to stand on the beam (32.00+0.00), while 6 out of 10 NRP-treated rats (NRP-5GG analogue D4A; SEQ ID NO: 2) performed the 7-step walk (score: 23.50+2.46). On day 17 all but one NRP-treated animals could perform the walk (21.70+ 1.43). In comparison, 6 out of 9 control animals were still unable to stand on the beam (30.78+0.78) (FIG. 9). On day 24 there was no longer a significant difference between the vehicle and NRP-treated group. Significance analysed with Two-way ANOVA followed by Bonferroni post-test adjustment.

Conclusions

We conclude that NRPs can preventing or attenuate the degeneration or death of peripheral neurons and are an effective prophylactic or therapeutic treatment for various forms of peripheral neuropathy.

Example 6

NRP Effects on Trophoblast Migration, Survival and Proliferation

Methods and Materials

Human trophoblast cells were isolated from term placentas with prior approval by the Ethics Committee of the University of Auckland and consent of the patients. The maternal decidua was removed, exposing the villous interior of the placenta. Pieces of villous tissue were cut out and washed thoroughly with PBS before digestion using 0.25% trypsin. The digest was then diluted in Locke Ringers Buffer and DNAase I. Digestion of connective tissue surrounding the placental cells was carried out while stirring the mixture with a magnetic stirrer at a temperature of 37° C. The process was repeated 8 times, with the last 6 supernatants being collected in a bottle containing fetal bovine serum (FBS). The digestion step produced a heterogeneous dispersed cell preparation. The pooled supernates was centrifuged for 7 minutes at 1200 rpm. The cell pellet was resuspended in PBS and centrifuged. This was followed by a 10-minute incubation in erythrocyte lysis buffer with an underlayer of FBS in the last 2 minutes, followed by centrifugation for 7 minutes. Cells were resuspended in M199 medium and recentrifuged.

Cells were then purified using a percoll gradient (5, 20, 30, 35, 40, 50 and 60%). The gradients were prepared with the 60% percoll on the bottom, with decreasing concentrations near the top of the gradient. Cells were introduced into the 5% percoll layer. The cells were centrifuged for 20 minutes at 1200G to separate trophoblasts from debris and other cell types, leaving a band of trophoblasts in the 40% percoll band. This band was collected, the cells washed in M199 medium centrifuged and finally counted and plated according to the methods of Keelan et al, 1998.

Cell Lines

Reagents

Dulbecco's modified Eagle medium (DMEM; 10566-016), F-12 nutrient mix (ham; 11765-062), fetal bovine serum (FBS; 10091-148), trypsin (25300-054), and PBS (14040-182) were purchased from Invitrogen, California, U.S.A.

Buffers and Solutions

Cell culture medium: DMEM/F-12 supplemented with 10% FBS.

Cell Culture

Choriocarcinoma cells (Jeg-3, BeWo and Jar; ATCC) were cultured under similar conditions in DMEM/F-12 cell culture medium in 75 cm2 flasks with filter tops (Raylab). Cells were allowed to adhere and grow in an incubator equilibrated in 95%/5% air/$CO_2$ to approximately 70% confluence, before being split every 2 to 3 days by addition of 2 ml of 1× concentrated trypsin-EDTA. After a centrifugation step for 5 min at 1100 rpm, cells were resuspended in 15 ml of fresh DMEM/F-12 in sterile tissue flasks and placed back in the incubator.

Experiment 1. Haptotactic Migration Assay

Haptotactic migration assays were used as described in the U.S. patent application Ser. No. 10/976,699 (incorporated herein fully by reference).

Boyden Chamber Assays

To investigate the chemoattractive effect of an NRP on trophoblasts, cells were plated in inserts of 12-well Boyden chambers (transwell plates; Biolab) in which a chamber has a bottom, sides and a porous membrane insert above the bottom. The membrane of the insert has pores sufficiently small so that cells cannot pass through merely due to the force of gravity. Thus, there is a space below the membrane and above the bottom of the chamber. Medium is placed in the chamber filled to a level above the membrane and cells are placed in the portion of the chamber above the membrane. Cells that migrate through the pores in the membrane enter the space between the membrane and the bottom of the chamber.

Under control conditions, the bottom of the chamber is not pre-coated with a putative chemoattractive agent. Under test conditions, a putative chemoattractive agent is coated, or placed, on the bottom of the chamber. De-adhesion and subsequent diffusion of the chemoattractive agent into the medium creates a gradient of decreasing concentration in the medium farther away from the bottom of the chamber. The chemoattractive agent can diffuse through the pores in the membrane, thereby providing a biologically detectable concentration within the pores of the membrane and above the membrane. Sensitive cells placed in the top of the Boyden chamber can react to the gradient of concentration of the chemoattractive agent and can migrate through the pores in the membrane and down to the bottom of the chamber, where they can adhere to the bottom surface of the chamber. Such cells can be identified using microscopy, either with or without RNA/DNA intercalating agent (also known as a "stain"; e.g., a fluorescent live stain Syto 24™, or fluorescein diacetate (FDA)), and can be identified using fluorescent microscopy. Non-sensitive cells do not react to the chemoattractant and do not migrate into the bottom of the chamber. Thus, the number of migratory cells can be quantified.

Fluorescent cells adhered to the bottom of the Boyden chamber on the laminin-containing matrix within 22 hrs as detected by the application of a fluorescent live stain.

Methods

Initial NRP Coating

Control wells of Transwell™ plates (Corning) with 12 μm pore size were coated in 1.5 ml of the bovine serum albumin/phosphate buffered saline (BSA/PBS) vehicle. Remaining plates were coated using various concentrations of NRP-5RG D6A analogue (SEQ ID NO: 1; 0.1 ng/ml prepared in PBS containing 10 ug/ml BSA). The plates were then incubated at 37° C. for 1 hr to coat. Wells were then rinsed 2× with 1 ml sterile PBS.

Extracellular Matrix Coating

Laminin (7 μg/ml) was used as an extracellular matrix (ECM) coating for the trophoblasts. All ECM compounds were diluted in PBS. 1.5 ml of the ECM per well was incubated for 2 hrs at room temperature. The wells were then rinsed once with 1 ml serum-free media (e.g. NB/B27) followed by 1 ml PBS wash.

Coating of Inserts

A 5 ug/mL PDL (Poly-D-Lysine)/PLL (Poly-L-Lysine) mixture (in PBS) was used to coat inserts. Subsequently the inserts were rinsed with distilled, deionised ("MilliQ™") water.

Transferring to Media and Cell Seeding

Appropriate medium was transferred into the 12-well plates. The plates were then incubated at 37° C.; 5% $CO_2$ and seeded with 50,000 cells in the presence of 100 fM NRP-5RG D6A (SEQ ID NO:1) in the inserts. After 20 hours the cells were incubated with 0.1 μg/ml Syto 24 for 2 h. Following that the plates were fixed.

Fixation

Inserts were discarded and wells fixed in successive dilutions of parafomaldehyde (PFA); (0.4, 1.2, 3 and 4%) for 3-5 min in each dilution. The wells were rinsed and stored in successive dilutions of PFA (0.4, 1.2, 3 and 4%) 3-5 min in each dilution. The wells were rinsed and stored in PBS until counting. All cells that displayed neurite outgrowth and traveled to the bottom chamber were counted as migrating cells.

Results

Figure 10:
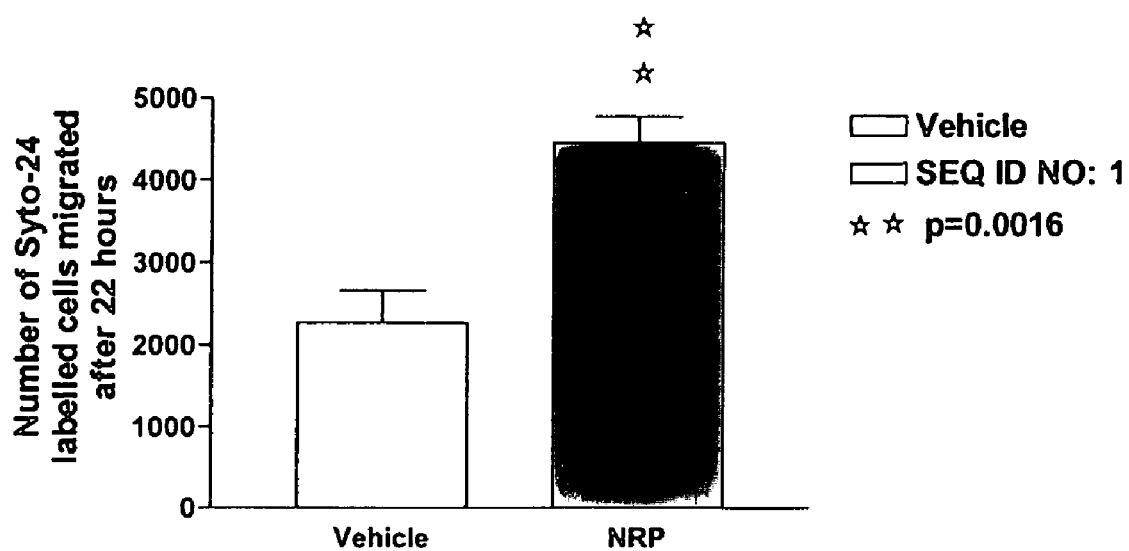
FIG. 10 shows that human primary trophoblast migration can be enhanced significantly by NRP application to the Boyden chamber assay. One-way ANOVA with Bonferroni posttest were used for statistical analysis of the data (☆☆ p=0.0016).

NRP treatment resulted in a 95% increase of migratory cells derived from a highly purified trophoblast-enriched primary human term placenta tissue fraction (FIG. 10).

Experiment 2: Trophoblast Survival Assay

In this series of experiments, we studied whether NRP-5RG D6A was able to protect purified primary placental trophoblasts against TNF-alpha mediated injury.

1. Effect of NRP on TNF-Alpha-Induced Cytotoxicity in Isolated Trophoblasts

In this study, we plated 30,000 freshly isolated trophoblast cells per well in microtiter well plates followed by pre-incubation with NRP-5RG D6A (SEQ ID NO: 1) for 24 hours. Then, we introduced 48 h injury with TNF-alpha (5 ng/ml; "low injury" or 50 ng/ml; "high injury") and interferon gamma (100 IU/100 μl). The results of the analysis of the cell survival are shown in FIG. 11.

Figure 11:
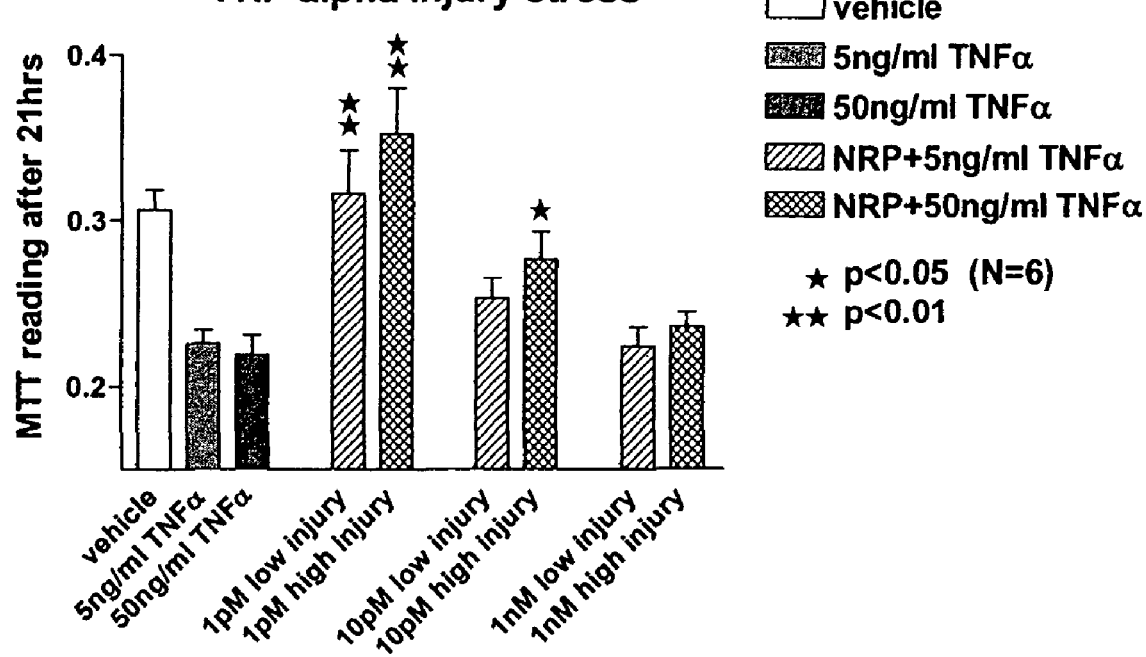
FIG. 11 shows that TNF-alpha mediated human trophoblast cytotoxicity can be prevented by pre-incubation with NRP. One-way ANOVA with Bonferroni posttest were used for statistical analysis of the data (☆ p<0.05; ☆☆ p<0.01).

FIG. 11 shows that 24 hrs pre-incubation of purified primary placental trophoblasts with NRP-5 analogue D6A (SEQ ID NO: 1) resulted in dose-dependent cytoprotection from TNF-alpha mediated injury, with 100% protection at a concentration of 1 pM. At a concentration of 10 pM, NRP was protective, but at a high concentration (1 nM), the effect of NRP was not statistically significant. The effect is very robust at two different applied concentrations of the toxin TNF-alpha.

2. Effects of NRP on TNF-Alpha-Induced Cytotoxicity in an Immortalized Trophoblast Cell Line In this study, we plated 50,000 JAr cells per well. JAr cells are an immortalized line of cells derived from a human choriocarcinoma cells. Wells were pre-incubated with NRP-5RG D6A (SEQ ID NO: 1) at the concentrations indicated in FIG. 12, or epidermal growth factor (EGF; 5 ng/ml) for 2 hours. Subsequently, cells were exposed to the cultures for 48 hours to TNF-alpha (5 ng/ml) and interferon-gamma (5 ng/ml) to induce stress. Results are shown in FIG. 12.

Figure 12:
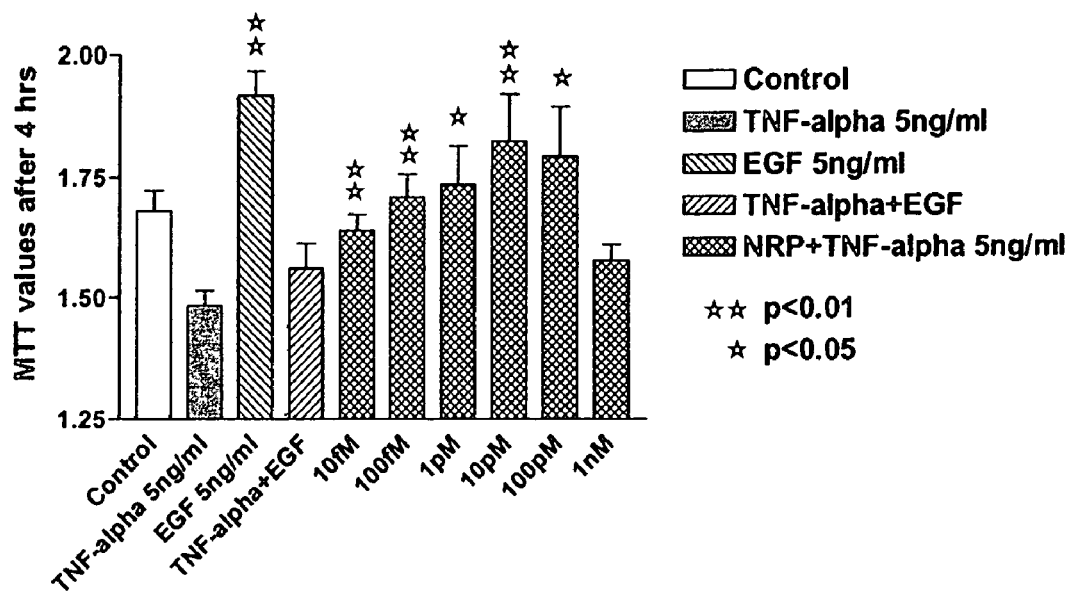
FIG. 12 shows that TNF-alpha mediated human trophoblast choriocarcinoma JAR cell line mediated cytotoxicity can be prevented in a dose-dependent fashion by pre-incubation with NRP. One-way ANOVA with Bonferroni posttest were used for statistical analysis of the data (☆ p<0.05; ☆☆ p<0.01).

FIG. 12 shows that EGF alone had only a weak effect to rescue JAr cells from TNF-alpha-induced cytotoxicity. As an internal control, we used the proliferation-inducing peptide EGF to show that under the conditions of the study, the cells could respond to a known proliferative agent. We found that EGF stimulated trophoblast proliferation in the absence of TNF-alpha injury. In contrast to the lack of a rescue effect of EGF, we unexpectedly found that NRP-5RG D6A (SEQ ID NO: 1) caused a concentration-dependent rescue effect, with a significant effect observed at a concentration of 10 fM and a maximal effect observed at a concentration of from about 1 pM to about 100 pM. Further increases in concentration (to 1 nM) produced a reduced rescue effect.

Experiment 3: Trophoblast Proliferation Assay

Cell proliferation was determined by BrdU incorporation to examine the effects of NRP-5RG D6A on the proliferation of trophoblasts. EGF ($0.8 \times 10^{-9}$ M) was used as a positive control, since studies have previously shown it plays a role in enhancing trophoblast proliferation (Maruo et al., 1992).

Initially cells were treated with NRP-5RG D6A (SEQ ID NO: 1), EGF and BrdU (0.05 μM) for 72 hrs. After the first 24 hrs, an 80% media change was carried out since BrdU is toxic over long incubation periods. Following 72 hrs of incubation, the reaction was stopped by fixation in 4% PFA. However, with this experimental design, most trophoblasts would form syncytia by the end of the 72 hrs, hindering accurate examination of the proliferative effect of NRP-5RG D6A on trophoblasts. Hence, the design was modified, and cells were fixed 24 hrs after treatment. This allowed analysis of proliferation of mononuclear trophoblasts.

Figure 13:
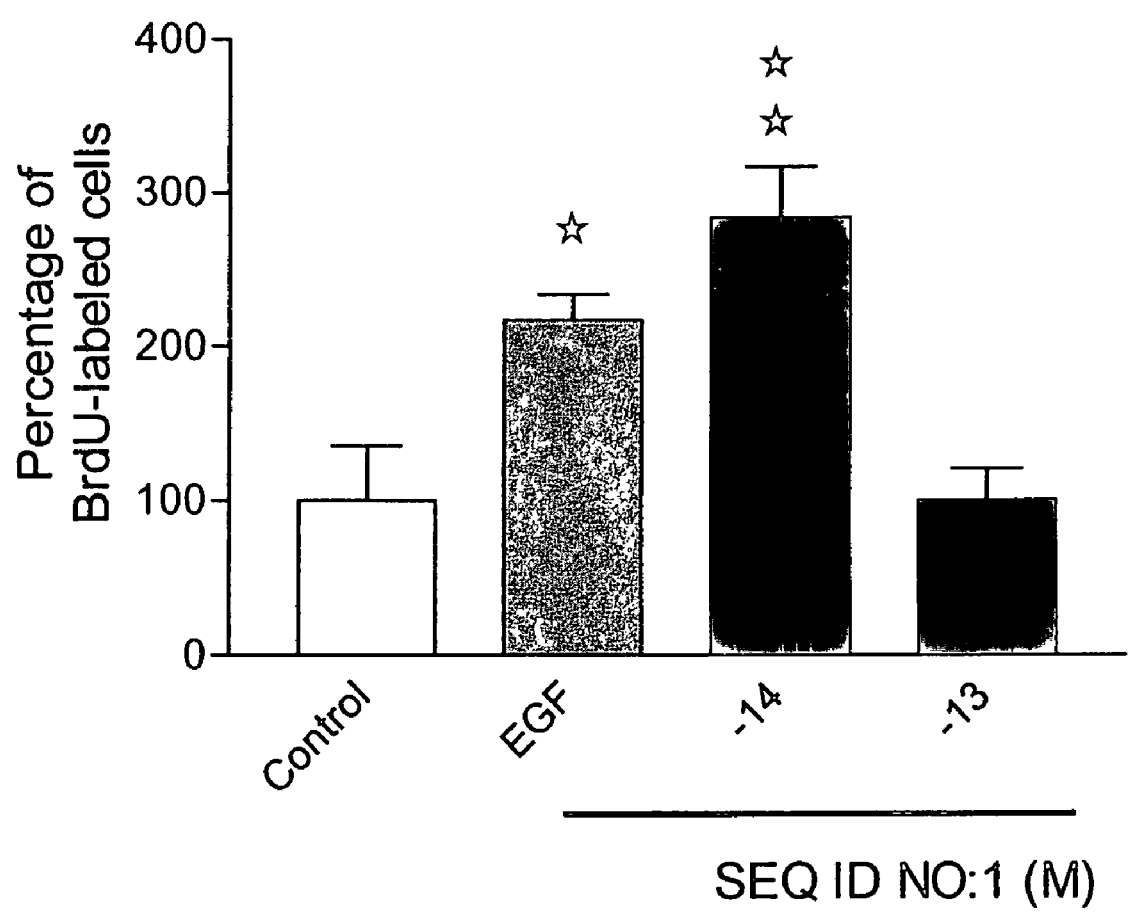
FIG. 13 shows that NRP-5 RG analogue D6A (SEQ ID NO: 1) caused a significant increase in trophoblast proliferation at $10^{-14}$M. Data shown are a percentage of mean values±SEM (normalized to control) of pooled replicates (n=4) from 1 experiment (* p<0.05, ** p<0.01; one-way ANOVA, using Bonferroni as post hoc test).

Treatment of primary human trophoblasts with NRP-5RG D6A resulted in a significant increase in trophoblast proliferation at $10^{-14}$ M (FIG. 13). NRP-5RG D6A showed a 183.3±50.2% increase in trophoblast proliferation at $10^{-14}$ M, while no increase in proliferation compared to the control was seen at $10^{-13}$ M. Higher concentrations were tested as well (data not shown), but no proliferative effect was detected at any NRP-5RG D6A concentration other than $10^{-14}$ M. EGF exerted an increase in trophoblast proliferation by 116.7±44% compared to control.

Results

DNA synthesis evaluation by BrdU uptake revealed that NRP-5RG D6A caused a significant increase in trophoblast proliferation at $10^{-14}$ M. EGF ($0.8 \times 10^{-9}$ M) was used as a positive control and demonstrated a significant increase in trophoblast proliferation. Cell proliferation was evaluated over 24 hrs after seeding $1.3 \times 10^5$ cells/cm$^2$ in culture media (1% serum) treated with 0.05 μM BrdU, NRP-5RG D6A and EGF (FIG. 13).

This invention is described with reference to specific embodiments thereof. Persons of ordinary skill can develop other embodiments based on the disclosures and teachings herein. All of those embodiments are considered to be part of this invention. All references cited herein are expressly incorporated fully by reference.

We claim:

1. An isolated neural peptide consisting of the sequence of REGRRAAPGRAGG (SEQ ID NO: 1) or GRRAAPGRAGG (SEQ ID NO:2).

2. The peptide of claim 1 where the C-terminus is amidated.

3. A formulation comprising a pharmaceutically acceptable amount of the peptide of claim 1 and pharmaceutically acceptable excipient.

4. The formulation of claim 3 including a stabilizer.

5. The formulation of claim 4 where the stabilizer is sucrose or trehalose.

6. The formulation of claim 5 where the stabilizer is present in a concentration of about 0.5 M.

* * * * *